US011319586B2

(12) United States Patent
Lo et al.

(10) Patent No.: US 11,319,586 B2
(45) Date of Patent: May 3, 2022

(54) SINGLE-MOLECULE SEQUENCING OF PLASMA DNA

(71) Applicant: The Chinese University of Hong Kong, Shatin (CN)

(72) Inventors: Yuk-Ming Dennis Lo, Homantin (CN); Rossa Wai Kwun Chiu, Shatin (CN); Suk Hang Cheng, Fanling (CN)

(73) Assignee: The Chinese University of Hong Kong, Shatin (HK)

( * ) Notice: Subject to any disclaimer, the term of this patent is extended or adjusted under 35 U.S.C. 154(b) by 69 days.

(21) Appl. No.: 15/235,630

(22) Filed: Aug. 12, 2016

(65) Prior Publication Data

US 2017/0044606 A1  Feb. 16, 2017

Related U.S. Application Data

(60) Provisional application No. 62/204,396, filed on Aug. 12, 2015.

(51) Int. Cl.
*C12Q 1/6874* (2018.01)
*C12Q 1/6869* (2018.01)
*C12Q 1/6806* (2018.01)
*G01N 33/487* (2006.01)
*G16B 30/00* (2019.01)
*G16B 30/10* (2019.01)

(52) U.S. Cl.
CPC ......... *C12Q 1/6874* (2013.01); *C12Q 1/6806* (2013.01); *C12Q 1/6869* (2013.01); *G01N 33/48721* (2013.01); *G16B 30/00* (2019.02); *C12Q 2521/501* (2013.01); *C12Q 2525/191* (2013.01); *C12Q 2565/631* (2013.01); *G16B 30/10* (2019.02)

(58) Field of Classification Search
CPC .. C12Q 1/6874; C12Q 1/6869; C12Q 1/6806; C12Q 2565/631; C12Q 2525/191; C12Q 2521/501; G01N 33/48721
See application file for complete search history.

(56) References Cited

U.S. PATENT DOCUMENTS

| 8,467,976 | B2 | 6/2013 | Lo et al. | |
|---|---|---|---|---|
| 8,620,593 | B2 | 12/2013 | Lo et al. | |
| 2009/0029377 | A1 | 1/2009 | Lo et al. | |
| 2012/0045771 | A1* | 2/2012 | Beier | C12N 15/1006 435/6.14 |
| 2013/0040824 | A1 | 2/2013 | Lo et al. | |
| 2013/0040827 | A1 | 2/2013 | Macevicz | |
| 2014/0100121 | A1 | 4/2014 | Lo et al. | |
| 2019/0123561 | A1 | 4/2019 | Kudo | |

FOREIGN PATENT DOCUMENTS

| CN | 103827320 A | 5/2014 | | |
|---|---|---|---|---|
| CN | 107002130 A | 8/2017 | | |
| EP | 1225234 A2 | 7/2002 | | |
| JP | 2008161056 A | 7/2008 | | |
| JP | 2015505458 A | 2/2015 | | |
| JP | 2018161056 A | 10/2018 | | |
| WO | 2006095169 A1 | 9/2006 | | |
| WO | 2010068289 A2 | 6/2010 | | |
| WO | 2012060595 A2 | 5/2012 | | |
| WO | WO-2013014451 A1 * | 1/2013 | ........... | C12Q 1/6869 |
| WO | 2013109970 A1 | 7/2013 | | |
| WO | 2013185137 A1 | 12/2013 | | |
| WO | 2014033455 A1 | 3/2014 | | |
| WO | 2014043763 A1 | 3/2014 | | |
| WO | WO-2015089333 A1 * | 6/2015 | ........... | C12Q 1/6869 |
| WO | WO-2016077313 A1 * | 5/2016 | ........... | C12Q 1/6869 |

OTHER PUBLICATIONS

Laszlo et al. Nature Biotechnology 2014; 32: 829-833 + Supplementary Information (Year: 2014).*
Proutski and Holmes. Bioinformatics 1998; 14: 467-468 (Year: 1998).*
Van den Oever et al. Clinical Chemistry 2013; 59: 4 (Year: 2013).*
Li et al. Detection of Paternally Inherited Fetal Point Mutations for Beta-Thalassemia Using Size-Fractionated Cell-Free DNA in Maternal Plasma. Journal of the American Medical Association 2005; 293: 843-849. (Year: 2005).*
International Search Report and Written Opinion dated Nov. 18, 2016 in PCT Application No. PCT/CN2016/094802. 12 pages.
Extended European Search Report dated Nov. 29, 2018 in EP Patent Application No. 16834683.1. 6 pages.
Timp, Winston et al.; "DNA Base-Calling from a Nanopore Using a Viterbi Algorithm"; Biophysical Journal (Biophysical Letters); May 2012; vol. 102, No. 10; doi: 10.1016/j.bpj.2012.04.009; pp. L37-L39.
Written Opinion (with Search Report) dated Mar. 5, 2019 in SG Patent Application No. 11201800888V. 13 pages.
Examination Report No. 1 dated Aug. 21, 2019 in AU Patent Application No. 2016305103. 4 pages.

(Continued)

*Primary Examiner* — Angela M. Bertagna
(74) *Attorney, Agent, or Firm* — Kilpatrick Townsend & Stockton LLP

(57) ABSTRACT

Embodiments may include a method of determining a nucleic acid sequence. The method may include receiving a plurality of DNA fragments. The method may also include concatemerizing a first set of the DNA fragments to obtain a concatemer. The method may include performing single-molecule sequencing of the concatemer to obtain a first sequence of the concatemer. In some embodiments, single-molecule sequencing may be performed using a nanopore, and the method may include passing the concatemer through a nanopore. A first electrical signal may then be detected as the concatemer passes through the nanopore. The first electrical signal may correspond to a first sequence of the concatemer. In addition, the method may include analyzing the first electrical signal to determine the first sequence. Subsequences of the first sequence may be aligned to identify sequences corresponding to each of the first set of the DNA fragments.

27 Claims, 18 Drawing Sheets

(56) References Cited

OTHER PUBLICATIONS

Communication pursuant to Article 94(3) EPC dated Oct. 18, 2019 in EP Patent Application No. 16834683.1. 4 pages.
English translation of Office Action dated Jun. 15, 2020 in IL Patent Application No. 257074. 3 pages.
English translation of Office Action dated Jun. 30, 2020 in JP Patent Application No. 2018-506601. 5 pages.
English translation of Office Action and Search Report dated Aug. 28, 2020 in TW Patent Application No. 105125873. 5 pages.
Communication pursuant to Article 94(3) EPC dated Oct. 19, 2020 in EP Patent Application No. 16834683.1. 4 pages.
Liu, Nannan et al.; "Two-Way Nanopore Sensing of Sequence-Specific Oligonucleotides and Small-Molecule Targets in Complex Matrices Using Integrated DNA Supersandwich Structures"; Angewandte Chemie International Edition; 2013; vol. 52, Issue 7; pp. 2007-2011.

* cited by examiner

SINGLE-MOLECULE SEQUENCING OF PLASMA DNA

CROSS-REFERENCE TO RELATED APPLICATION

This application claims the benefit of priority to U.S. Provisional Application No. 62/204,396, filed Aug. 12, 2015, the contents of which are incorporated herein by reference for all purposes.

BACKGROUND

Noninvasive prenatal testing (NIPT) by maternal plasma DNA sequencing is now clinically available for screening fetal chromosomal aneuploidies (1). Unlike amniocentesis, maternal plasma DNA sequencing does not pose any miscarriage risk. These tests have close to 99% sensitivity and 99% specificity (1). Consequently, the clinical demand for NIPT has increased substantially since it first became commercially available in 2011.

Massively parallel sequencing is a core component of most of the currently used laboratory protocols for NIPT of chromosomal aneuploidies (2). Due to the high instrumentation cost, those tests are currently performed at reference laboratories. OXFORD NANOPORE TECHNOLOGIES® has developed a nanopore-based DNA sequencing platform (3). Nanopore sequencers have a comparatively low equipment cost and have a small footprint. Each flow cell costs US$500-900 and can be used for multiple times for up to 48 hours. The sequencing speed is also relatively fast that can read 30 bases per second from each nanopore. Such features would be advantageous for use in clinical laboratories. But, current nanopore techniques are inefficient for samples (e.g., plasma) typically used for NIPT.

BRIEF SUMMARY

Embodiments improve the efficiency of single-molecule sequencing techniques when analyzing samples with relatively small DNA fragments. For example, a concentration of DNA fragments in a sample can be increased significantly, thereby allowing more DNA fragments to interact with a sequencing device (e.g., a nanopore). As another example, DNA fragments are combined into concatemers to make longer molecules that can be read, thereby allowing multiple DNA fragments (i.e., DNA fragments originally in the sample) to be efficiently read via the sequencing of one molecule. Bioinformatic procedures can be used to detect the different DNA fragments that are part of a same concatemer. Embodiments can also combine the two techniques.

Embodiments may include a method of determining a nucleic acid sequence. The method may include receiving a plurality of DNA fragments. The method may also include concatemerizing a first set of the DNA fragments to obtain a first concatemer. The method may include performing single-molecule sequencing of the first concatemer to obtain a first sequence of the first concatemer. In some embodiments, single-molecule sequencing may be performed using a nanopore, and the method may include passing the first concatemer through a first nanopore. A first electrical signal may then be detected as the first concatemer passes through the first nanopore. The first electrical signal may correspond to a first sequence of the first concatemer.

Other embodiments may include a method of determining a nucleic acid sequence. The method may include receiving a plurality of DNA fragments. A first set of DNA fragments may be concatemerized to obtain a first concatemer. A fluorescent-labeled nucleotide may be hybridized to the concatemer. A first fluorescent signal may be detected, with the first fluorescent signal corresponding to a specific nucleotide. The fluorescent label may then be cleaved away and another fluorescent-labeled nucleotide may be added, and the process may be repeated.

Embodiments may include a method performed by a computer system. The method may include receiving a first sequence of a first concatemer generated by concatemerizing a first set of DNA fragments. The method may also include aligning subsequences of the first sequence to identify fragment sequences corresponding to each DNA fragment of the first set of the DNA fragments.

Some embodiments may include a method of sequencing cell-free DNA fragments. Cell-free DNA fragments may include plasma DNA fragments. The method may include receiving a biological sample including a plurality of DNA fragments. The biological sample may have a first concentration of DNA fragments. The method may also include concentrating the biological sample to have a second concentration of DNA fragments. The second concentration of DNA fragments may be 5 or more times higher than the first concentration of DNA fragments. The method may further include passing the plurality of DNA fragments through nanopores on a substrate. For each of the plurality of DNA fragments, electrical signals may be detected as the DNA fragment passes through a nanopore. The electrical signals may correspond to the sequence of the DNA fragment.

Embodiments may include a method of sequencing cell-free DNA fragments. The method may include concentrating a biological sample to have a second concentration of DNA fragments 5 or more times higher than an initial concentration of DNA fragments. The method may further include a single-molecule sequencing technique. The DNA fragment may be hybridized with a fluorescent-labeled nucleotide. The method may also include detecting a signal from the fluorescent-labeled nucleotide, with the signal corresponding to the nucleotide. The fluorescent-labeled nucleotide may be cleaved off, and the process may be repeated to identify additional nucleotides and a sequence of the DNA fragment.

Embodiments may also include a computer product that includes a computer readable medium that stores a plurality of instructions to perform an operation of any of the methods of sequencing DNA described herein. Some embodiments may include a computer product and one or more processors for executing instructions stored on the computer readable medium. Additional embodiments include systems to perform any of the methods.

Other embodiments are directed to systems, portable consumer devices, and computer readable media associated with methods described herein.

A better understanding of the nature and advantages of embodiments of the present invention may be gained with reference to the following detailed description and the accompanying drawings.

TERMS

Figure 1A:
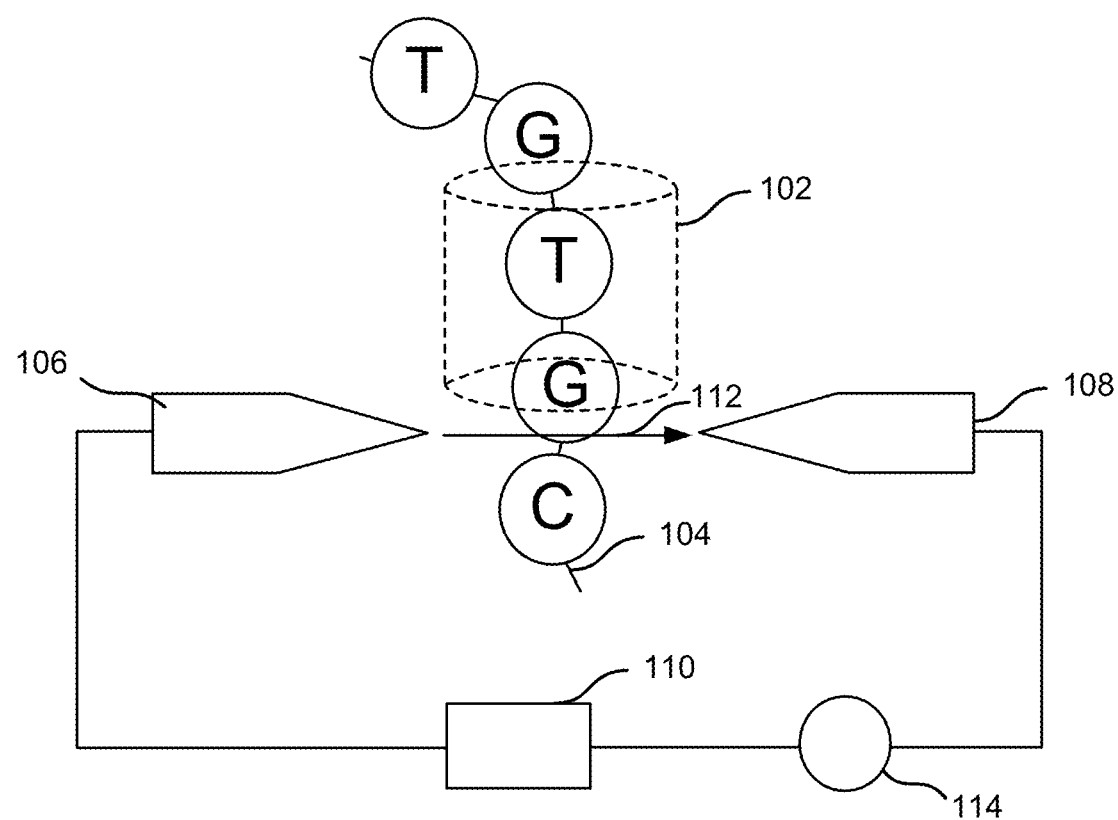
FIG. 1A shows a simplified diagram of a nanopore device and a nucleic acid according to embodiments of the present invention.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (mother vs. fetus) or to healthy cells vs. tumor cells.

A "biological sample" refers to any sample that is taken from a subject (e.g., a human, such as a pregnant woman, a person with cancer, or a person suspected of having cancer, an organ transplant recipient or a subject suspected of having a disease process involving an organ (e.g., the heart in myocardial infarction, or the brain in stroke, or the hematopoietic system in anemia) and contains one or more nucleic acid molecule(s) of interest. The biological sample can be a bodily fluid, such as blood, plasma, serum, urine, vaginal fluid, fluid from a hydrocele (e.g. of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g. thyroid, breast), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at for example, 30,000 g for another 10 minutes to remove residual cells. The cell-free DNA in a sample can be derived from cells of various tissues, and thus the sample may include a mixture of cell-free DNA.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

A "concatemer" is a continuous DNA molecule composed of separate DNA fragments that have been combined into the single molecule. Various ones of the separate DNA fragments of the concatemer may or may not have a same sequence. At least some of the DNA fragments in a concatemer may have different sequences. The separate DNA fragments used to make the concatemer can be derived from various tissues that exist in a biological sample, e.g., when the DNA fragments are cell-free DNA fragments, as may occur in plasma and other cell-free DNA mixtures.

A "sequence read" refers to a string of nucleotides sequenced from any part or all of a nucleic acid molecule. For example, a sequence read may be the entire nucleic acid fragment that exists in the biological sample. A sequence read may be obtained from a single-molecule sequencing. "Single-molecule sequencing" refers to sequencing of a single template DNA molecule to obtain a sequence read without the need to interpret base sequence information from clonal copies of a template DNA molecule. The single-molecule sequencing may sequence the entire molecule or only part of the DNA molecule. A majority of the DNA molecule may be sequenced, e.g., greater than 50%, 55%, 60%, 65%, 70%, 75%, 80%, 85%, 90%, 95%, or 99%.

For sequencing, a "signal" can refer to a measurement taken at an instant in time. Examples of such signals include an optical signal or an electrical signal. An optical signal can provide an image corresponding to a particular color corresponding to a particular base, e.g., when hybridization occurs. A single image may be of an array of sequencing devices (e.g., a nanopore or other sequencing volume), thereby having the single image be of many optical signals. An electrical signal can be a measurement across electrodes at an instant in time. The electrical signals of a time period can provide one or more bases in a sequence of a DNA molecule. The electrical signal may include a current or a voltage signal.

A "nanopore" refers to an opening into which a molecule or part of a molecule can be placed, where a signal can be detected based on one or more properties of the part of the molecule that is in the nanopore. A nanopore can be composed of various materials, such as polymers, metals or other solid-state materials, proteins, or combinations thereof.

A "classification" refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1). The term "cutoff" and "threshold" refer to a predetermined number used in an operation. For example, a cutoff size can refer to a size above which fragments are excluded. A threshold value may be a value above or below which a particular classification applies. Either of these terms can be used in either of these contexts.

The term "chromosome aneuploidy" as used herein means a variation in the quantitative amount of a chromosome from that of a diploid genome. The variation may be a gain or a loss. It may involve the whole of one chromosome or a region of a chromosome.

The term "sequence imbalance" or "aberration" as used herein means any significant deviation as defined by at least one cutoff value in a quantity of the clinically relevant chromosomal region from a reference quantity. A sequence imbalance can include chromosome dosage imbalance, allelic imbalance, mutation dosage imbalance, copy number imbalance, haplotype dosage imbalance, and other similar imbalances. As an example, an allelic imbalance can occur when a tumor has one allele of a gene deleted or one allele of a gene amplified or differential amplification of the two alleles in its genome, thereby creating an imbalance at a particular locus in the sample. As another example, a patient could have an inherited mutation in a tumor suppressor gene. The patient could then go on to develop a tumor in which the non-mutated allele of the tumor suppressor gene is deleted. Thus, within the tumor, there is mutation dosage imbalance. When the tumor releases its DNA into the plasma of the patient, the tumor DNA will be mixed in with the constitutional DNA (from normal cells) of the patient in the plasma. Through the use of methods described herein, mutational dosage imbalance of this DNA mixture in the plasma can be detected. An aberration can include a deletion or amplification of a chromosomal region.

The term "size profile" generally relates to the sizes of DNA fragments in a biological sample. A size profile may be a histogram that provides a distribution of an amount of DNA fragments at a variety of sizes. Various statistical parameters (also referred to as size parameters or just parameter) can be used to distinguish one size profile to another. One parameter is the percentage of DNA fragment of a particular size or range of sizes relative to all DNA fragments or relative to DNA fragments of another size or range.

DETAILED DESCRIPTION

Embodiments can improve the efficiency of single-molecule sequencing when applied to cell-free DNA fragments in a biological sample (e.g., in plasma or serum), which are relatively short fragments of ~200 bases. Because cell-free DNA fragments, such as plasma DNA fragments are small or short and are typically present at low concentrations in a biological sample, use of a nanopore to sequence cell-free DNA fragments may not be expected to provide accurate results. Small fragments passing through a small pore make sequencing the fragment while the fragment is in the nanopore difficult. In addition, with a small fragment, alignment to a reference genome may be more difficult given expected sequencing errors. Nanopore sequencing may have sequencing errors of about 10-15%. In embodiments, the efficiency can be improved by concatemerization of DNA fragments to create longer molecules to be sequenced. In other embodiments, the efficiency can be improved by increasing the concentration of DNA fragments in the sample.

Without these developments, single-molecule sequencing on plasma DNA may not be practical. With these approaches, a range of plasma DNA aberrations were detectable by single molecule sequencing. Embodiments can be applied to many areas in medicine, including prenatal diagnosis, cancer assessment, inflammatory disease management, autoimmune disease assessment, and acute medicine, such as trauma. Furthermore, it has been reported that methylated cytosines could be distinguished from unmethylated cytosines by single molecule sequencing (12). We have previously reported that by detecting the methylation profile of plasma DNA, we were able to determine the fetal DNA fraction, detect pregnancy associated diseases with aberrant placental methylation profile, detect aberrant methylation associated with cancer and systemic lupus erythematosus (7, 9, 11). Accordingly, embodiments can also be used in applications detecting methylation.

I. SINGLE MOLECULE SEQUENCING OF DNA FRAGMENTS

Plasma or serum DNA are cell-free nucleic acid molecules found in the circulation of human subjects and are released during the process of cell death, both as part of natural turnover or pathological processes. Because the DNA molecules are released into the circulation as part of the cell degradation process, they circulate in the form of short fragments (<200 bp) and are present at low concentrations. It is known the majority of plasma DNA in healthy subjects originate from hematological cells (6).

During pregnancy, the placenta contributes plasma DNA molecules into the maternal circulation and offers a means to access fetal DNA for non-invasive prenatal diagnosis (7). Tumors and cancers have high cell turnover rates and contribute DNA into plasma where the chromosomal and genetic abnormalities could be detected non-invasively and serve as a liquid biopsy for cancer diagnosis, monitoring, screening and prognostication (8, 9). Inflammatory conditions, such as myocardial infarction, stroke, hepatitis and others also result in increased plasma DNA contributions from the inflamed organs (10). Autoimmune diseases, such as systemic lupus erythematosus, are also associated with plasma DNA abnormalities (11). In the above mentioned diseases, the plasma DNA profile may show single nucleotide variants associated with the disease, chromosome or subchromosomal copy number aberrations (copy number gains or losses, aneuploidies), aberrant methylation (hypermethylation or hypomethylation) and size profile abnormalities (extra amounts of short or extra amounts of long DNA molecules). In summary, circulating cell-free DNA analysis has become an important means for the development of molecular diagnostic tests for a wide range of diseases.

Single molecule sequencing, not limited to the format manufactured by OXFORD NANOPORE TECHNOLOGIES®, is an attractive platform for DNA sequencing analysis because of the high speed at which each DNA base could be identified. The workflow for library construction is simplified because the amplification steps are obviated. It can sequence continuous stretches of DNA, up to hundreds of kilobases. However, such advantages are not readily applicable to plasma DNA analysis. First, plasma DNA molecules are short fragments, mostly <200 bp in length. The DNA concentration in plasma and serum is substantially lower than that in tissue biopsies. Therefore, when a plasma DNA sample is applied to the nanopore sequencer, the sequencing efficiency was low. In other words, the DNA in the sample was too dilute and a plasma DNA molecule too infrequently found its way towards a nanopore. Even when a plasma DNA molecule found its way to a nanopore and got sequenced, due to its short length, the sequenced information only provided an extremely small amount of information with respect to the human genome. The haploid human genome is $3.3 \times 10^9$ bases in size. Moreover, one would expect the sequencing error rate using nanopores to make sequencing of short DNA fragments even less accurate than when sequencing long DNA fragments. Thus, we aimed to develop approaches to increase the frequency or chance whereby a plasma DNA molecule could be processed by the nanopores and other single-molecule sequencing devices.

A. Nanopore Sequencing

Nanopore sequencing is a form of single molecule sequencer where DNA bases are detected through the use of nanopores. OXFORD NANOPORE TECHNOLOGIES® uses protein pores, alpha-hemolysin. A matrix of such pores are fabricated to sit on a membrane (5). In addition to protein pores, a nanopore may be a solid state nanopore, where the nanopore is fabricated in semiconductor materials, including silicon compounds, such as silicon nitride, and graphene. Each pore may be connected to an electrical circuit.

FIG. 1A shows a simplified diagram of a nanopore 102 and a DNA molecule 104 according to embodiments of the present technology. Electrode 106 and electrode 108 may define part of the nanopore or may be located near the nanopore. Electrode 106 and electrode 108 are shown as having an end that may be conical or triangular. In some embodiments, electrodes may have a different shape. For example, the electrodes may have a flat end, a hemispherical end, or a rounded end. Both electrodes may not have the same shape. For example, one electrode may have a conical end and the other electrode may be flat. The distance between the electrodes may be equal to, less than, or greater than the diameter or width of the nanopore. Electrode 106 and electrode 108 may be connected to a power source 110. A current 112 may tunnel from electrode 106 to electrode 108. Power source 110 may be in electrical communication with a plurality of nanopores and a respective pair of electrodes.

When DNA molecule 104 passes through nanopore 102, there would be a change in current, which may be measured by meter 114. The different DNA bases, namely A, C, G, T would induce a different magnitude in current change. By observing the voltage or current pattern of each nanopore, the sequence of DNA molecule 104 that had passed through nanopore 102 could be determined. Because the sequencing is sensitive enough to detect DNA bases on a single molecule of DNA, i.e. does not require amplification of the DNA sequencing libraries, the speed of sequence detection is substantially enhanced.

However, a drawback is that the accuracy of the DNA base identification is relatively poorer than sequencing technologies that detect consensus sequences from amplified clones of each DNA molecule, such as ILLUMINA® sequencing. However, it has been shown that the base detection accuracy is substantially improved when 2D reads are interpreted (3). When preparing the DNA sample for nanopore sequencing, a hairpin adaptor is added to one end of each double-stranded DNA molecule. When such a DNA molecule approaches the nanopore, the double-strand would strip apart and one end of the now single-stranded DNA molecule would pass through the nanopore when the current changes could be detected. When the sequencing is nearing the end of this single-end, the complementary strand linked by the hairpin would continue to be passed through the nanopore and gets sequenced. When both strands of a DNA molecule is sequenced, a consensus sequence could be derived and this is termed a 2D read. As reported in the literature, 2D reads have higher base calling accuracy than 1D reads (sequences interpreted from a single strand only).

B. Other Single-Molecule Sequencing

Embodiments may also include single-molecule sequencing techniques other than techniques using nanopores. For example, with a Helicos Single Molecule sequencer (SEQLL®), DNA molecules may be hybridized onto a glass surface. A fluorescent-labeled nucleotide may then be added to each DNA molecule, and an image may be captured. The fluorescent molecule may then be cleaved away and washed away and another fluorescent-labeled nucleotide may be added and the process repeated. Each nucleotide may have a different fluorescent label, allowing the DNA to be sequenced.

Another example may include the PACIFIC BIOSCIENCES® single-molecule real-time (SMRT®) sequencing method. In this method, a DNA polymerase enzyme may be affixed to the bottom of a zero-mode waveguide (ZWM). The polymerase may then capture a single molecule of DNA. A fluorescent-labeled nucleotide may then be incorporated to the DNA-enzyme complex. A detector may then detect the fluorescent signal, and a base call may be made.

The fluorescence tag may then be cleaved and may diffuse out of the ZWM. The process may be repeated, with each type of nucleotide having a different fluorescent label, allowing the DNA to be sequenced.

II. INCREASING EFFICIENCY

To increase efficiency, one option is to amplify the plasma DNA pool to increase the amount of genetic material in the sample within the finite volume to be applied to the sequencing chamber or flow cell. However, the adoption of such a protocol would mean that one is no longer performing single-molecule sequencing, as now one would be sequencing the original DNA template and all of the replicated DNA fragments. Such a use of the replicated DNA fragments can cause errors when trying to obtain quantitative information about the original DNA fragments, e.g., copy number of the original DNA fragments in a given genomic region, such as a whole chromosome.

In the sections below, two approaches to increase efficiency are described. In one approach, DNA fragments may be concatenated to form a concatemer before performing single-molecule sequencing. In another approach, DNA fragments are highly concentrated in a sample before single-molecule sequencing (e.g., before nanopore sequencing).

A. Concatemers

Figure 1B:
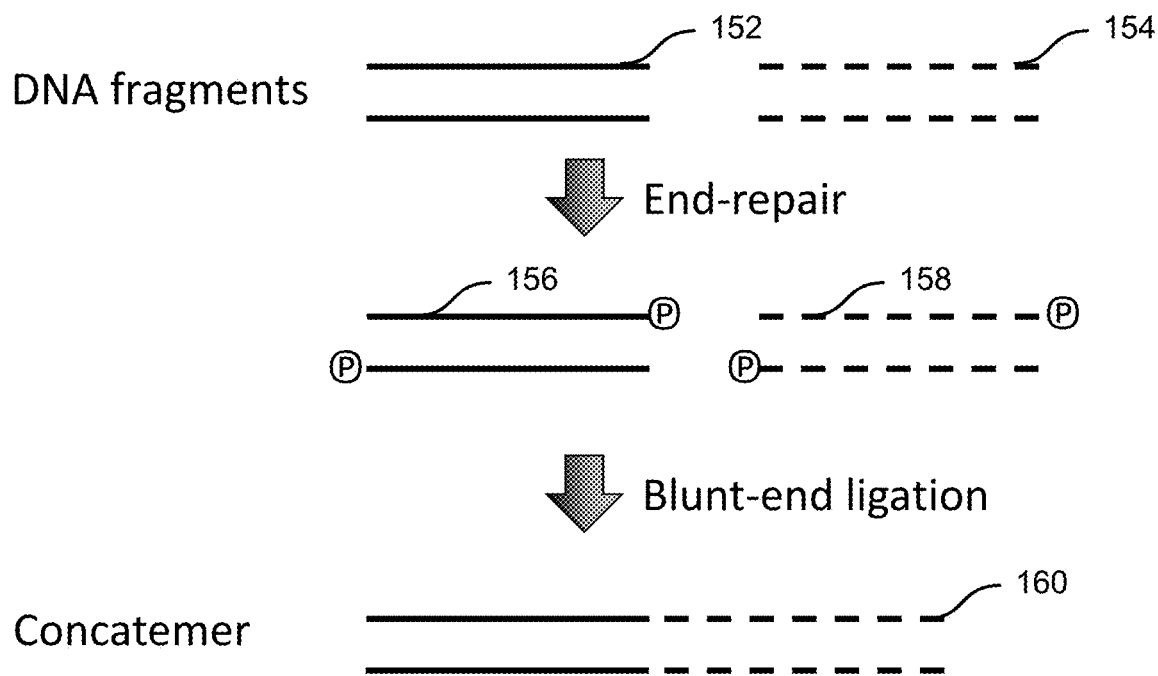
FIG. 1B illustrates the process of concatemerizing DNA fragments according to embodiments of the present invention.

In some embodiments, DNA fragments (e.g., plasma DNA fragments) may be concatemerized, as shown in FIG. 1B. The concatemerization can attach a series of DNA fragments to each other. For example, DNA fragment 152 and DNA fragment 154 may exist in a sample. As an initial procedure for attaching the DNA fragments to each other, the ends of DNA fragment 152 and DNA fragment 154 may be prepared with a phosphate group added to the ends, resulting in DNA fragment 156 and DNA fragment 158. The DNA fragments may then be linked together by ligase enzymes in blunt-end ligation to form a long DNA molecule, for example, concatemer 160. Concatemer 160 can be considered a new molecule that is a combination of the DNA fragments 152 and 154. Concatemer 160 will have a sequence that is a combination of the subsequences corresponding to DNA fragments 152 and 154.

Figure 2:
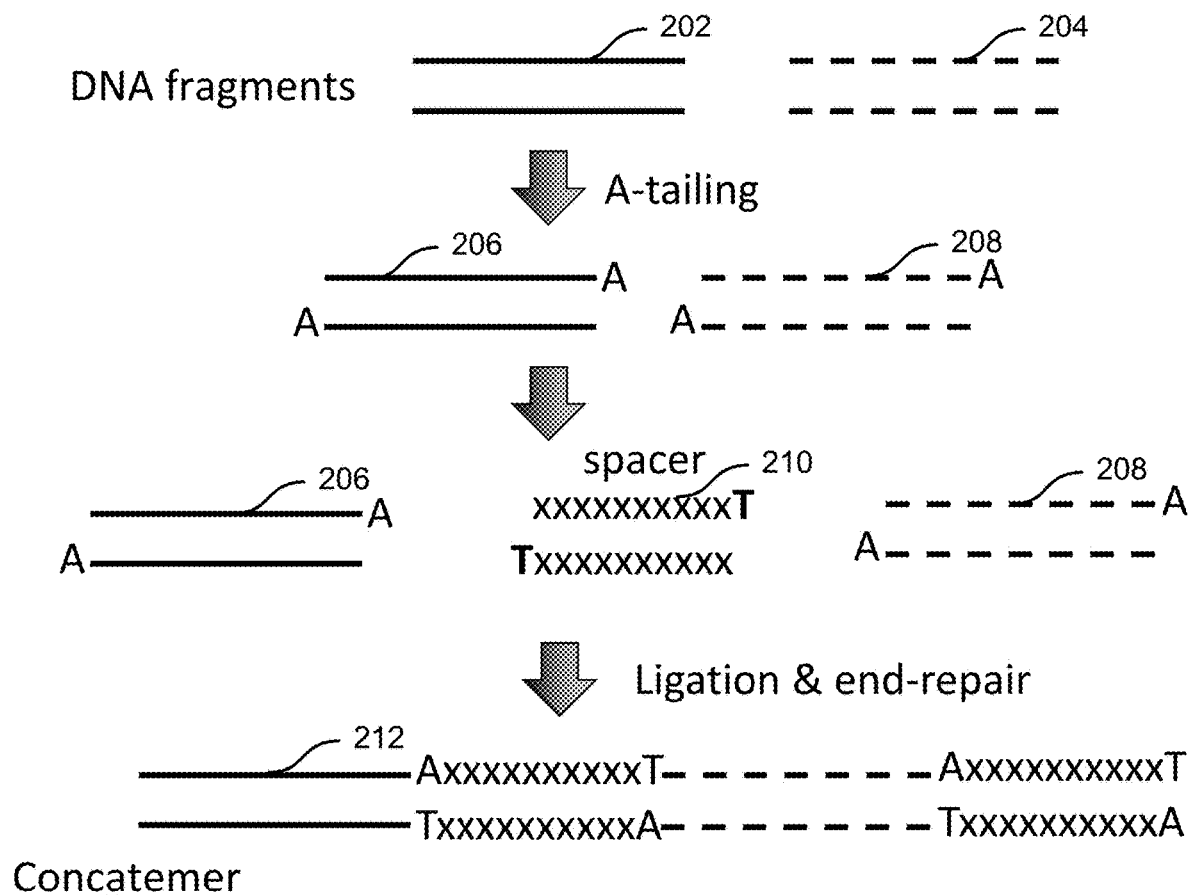
FIG. 2 depicts the process of concatemerizing DNA fragments along with spacer DNA fragments according to embodiments of the present invention.

FIG. 2 shows a similar approach of forming concatemers, with spacer fragments (also just called "spacers") between DNA fragments. DNA fragment 202 and DNA fragment 204 may undergo "A-tailing," where an A nucleotide may be added to one end of each strand of the DNA fragment, forming DNA fragment 206 and DNA fragment 208. A spacer DNA fragment 210 may have a known sequence with a T nucleotide on one end of each strand of the spacer DNA fragment. The known sequence of spacer DNA fragment may be under 20 base pairs, including from 4 to 10 base pairs and from 10 to 20 base pairs, not including the A or T nucleotides added onto the ends of the spacer fragments. Other complementary nucleotides may be used as well at the ends of the spacer DNA fragment and the plasma DNA fragment. Spacer DNA fragment 210 may then linked to DNA fragment 206 and DNA fragment 208 by ligase enzymes to form a long DNA molecule shown as concatemer 212. A spacer DNA fragment may be placed between two DNA fragments that are not spacers. For example, one spacer DNA fragment may be between two DNA fragments extracted from the biological sample. Concatemer 212 may have a sequence that is a combination of sequences corresponding to DNA fragments 206 and 208 along with one or more of spacer DNA fragment 210.

In some embodiments, the spacer fragments can indicate the end of one DNA fragment and the beginning of another DNA fragment, e.g., when the known sequence of the spacer fragments does not appear in a reference genome corresponding to the subject (e.g., a human genome) or appears less than a specific number of times (e.g., less than 2 or 3). A computer system can identify a sequence of a spacer fragment by comparing subsequences to an expected set of one or more known sequences used for the spacer fragments. In some implementations, the spacer fragments can just be the A-T combination at a single position. In such implements, the use of A and T may be mainly for attachment as opposed to any identification of when the DNA fragments start and end.

Methods with a spacer may include identifying a starting base of a subsequence corresponding to a DNA fragment of the biological sample. Identifying the starting base may be based on identifying one of the known sequences of the spacer DNA fragment. The ending based of the subsequence may be identified based on identifying one of the known sequences of the spacer DNA fragment after the subsequence.

With these approaches, when the long molecule (the concatemer) reaches a nanopore, many plasma DNA fragments may be sequenced because the concatemer may include several plasma DNA fragments in a single long molecule. Because the plasma DNA molecules may be naturally double-stranded, a hairpin adaptor may be applied at the end of the concatemer so that 2D reads can be generated, i.e., both strands are read. After sequencing, the original units of plasma DNA molecules incorporated into the concatemer may be identified. Creating a long molecule out of several DNA fragments and sequencing the long molecule in the nanopore provides greater efficient than waiting for the same several molecules to separately move into nanopores to be sequenced.

1. Use in Single-Molecule Sequencing

Figure 3A:
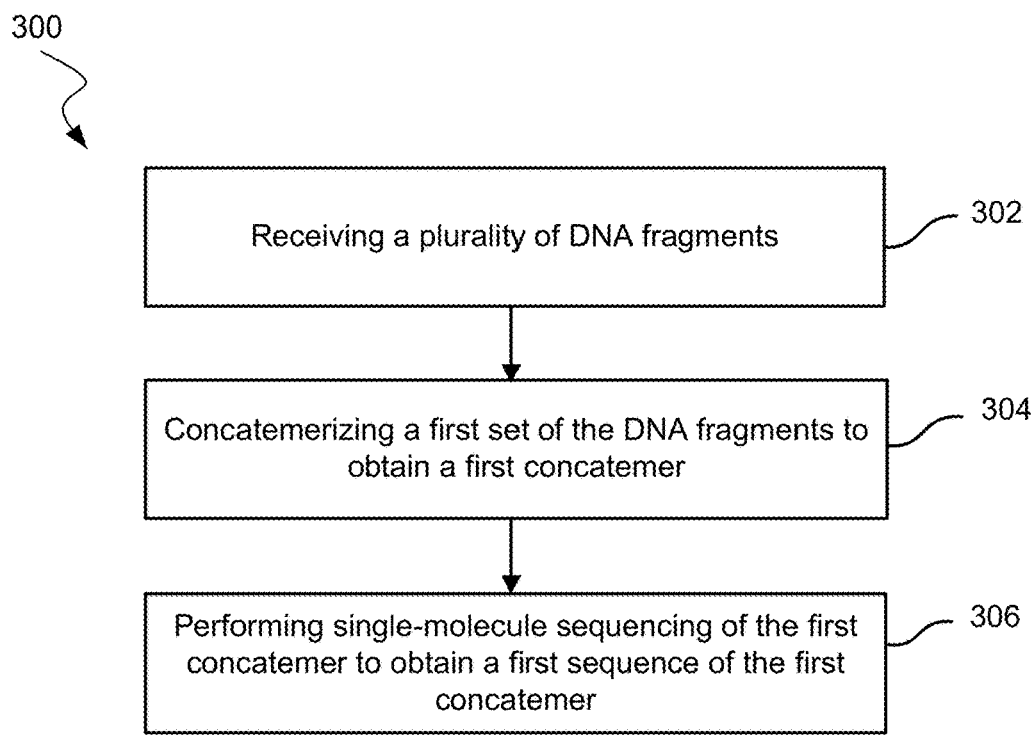
FIG. 3A shows a simplified block flow diagram of a method of sequencing DNA fragments by concatemerizing the DNA fragments and using single-molecule sequencing according to embodiments of the present invention.

FIG. 3A shows a simplified block flow diagram of a method 300 of sequencing DNA fragments by concatemerizing the DNA fragments and using single-molecule sequencing according to embodiments of the present invention.

At block 302, method 300 may include receiving a plurality of DNA fragments. The plurality of DNA fragments may be cell-free DNA fragments from a biological sample. The biological sample may be plasma or serum. The DNA fragments may be separated from other components of the biological sample, e.g., as plasma is separated from other components of blood. The DNA fragments may be any DNA fragments described herein.

At block 304, method 300 may include concatemerizing a first set of the DNA fragments to obtain a first concatemer. Concatemerizing may be by any method described herein. The first concatemer can include DNA fragments other than the first set. Thus, the first set of DNA fragments may not be all of the DNA fragments that compose the first concatemer. Other DNA fragments in the first concatemer may include spacer DNA fragments.

Block 306 shows that method 300 may also include performing single-molecule sequencing of the first concatemer to obtain a first sequence of the first concatemer. Single-molecule sequencing may include nanopore sequencing. The first concatemer may be provided to a sequencing device as part of performing the single-molecule sequencing. The sequencing device may be a nanopore device, an optical waveguide, a flow cell configured so that the concatemer hybridizes onto the flow cell, or any reaction cell or location where sequence detection of a single DNA molecule takes place. An example of a flow cell may include a flow cell with an oligonucleotide adhered to the surface of the flow cell, where the oligonucleotide may hybridize with the first concatemer. Method 300 may further include detecting, using the sequencing device, a plurality of signals corresponding to the first concatemer. The plurality of signals may correspond to the first sequence of the first concatemer. The signals may include signals from fluorescent labels or other labels with optically detectable signals bonded to the first concatemer. The signals from fluorescent labels may be detected by optical detectors, lasers, charge-coupled devices, zero-mode waveguides, other optically sensitive devices that can determine the presence or absence of an optical event, or combinations thereof.

2. Detecting Electrical Signals in Nanopores

Figure 3B:
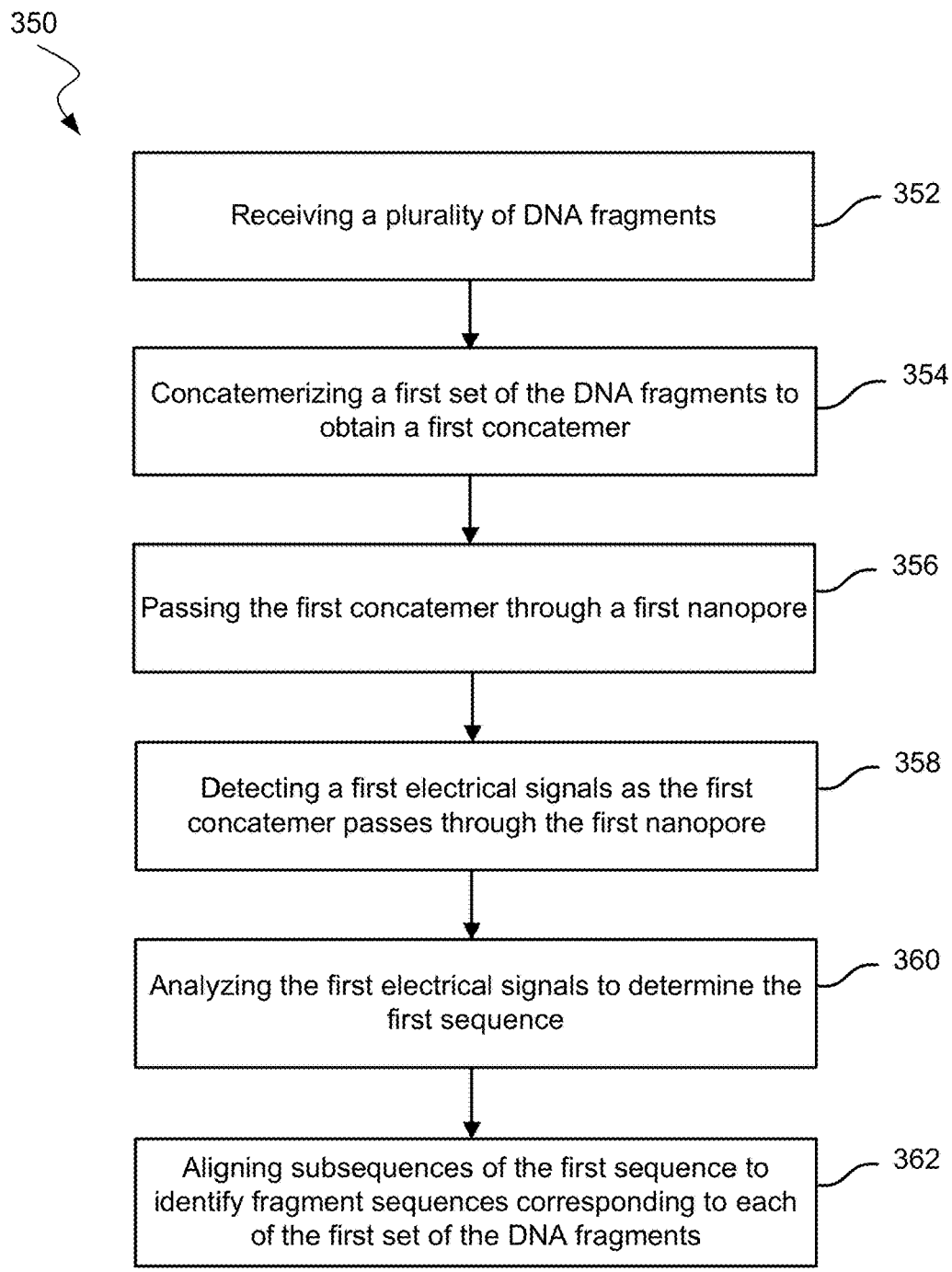
FIG. 3B shows a simplified block flow diagram of a method of sequencing DNA fragments using nanopore sequencing according to embodiments of the present invention.

FIG. 3B shows a simplified block flow diagram of a method 350 of sequencing DNA fragments using nanopore sequencing according to embodiments of the present invention. In method 350, the sequencing device is a nanopore, which may exist in an array of nanopores on a substrate. Aspects of method 350 can be performed when implementing method 300.

At block 352, method 350 may include receiving a plurality of DNA fragments. The plurality of DNA fragments may be cell-free DNA fragments from a biological sample. The biological sample may be plasma or serum. The DNA fragments may be separated from other components of the biological sample, e.g., as plasma is separated from other components of blood.

The DNA fragments may be received at a container that is used for concatemerizing. The container may be a vial or a tube, such as an Eppendorf tube. The DNA fragments may be mixed in the container with ligase enzymes and buffers.

Block 354 shows that method 350 may also include concatemerizing a first set of the DNA fragments to obtain a first concatemer. Concatemerizing may be by any method described herein. The first concatemer can include other DNA fragments than the first set. Thus, the first set of DNA fragments may not be all of the DNA fragments that compose the first concatemer.

Multiple concatemerizing processes may be performed in parallel, with each process forming a separate concatemer. The various concatemers can be of different lengths, e.g., because the different DNA fragments can be of different lengths and because varying numbers of DNA fragments can be incorporated into a concatemer. For example, one concatemer can be composed of 3 DNA fragments and another concatemer can be composed of 100 DNA fragments.

In block 356, method 350 may further include passing the first concatemer through a first nanopore. The first nanopore may be one of a plurality of nanopores on a substrate. Passing the first concatemer through a first nanopore may include passing a first strand of the first concatemer through the nanopore. After the first strand passes through the nanopore, a second strand of the first concatemer may pass through the nanopore. The first strand and the second strand may be connected by a hairpin adaptor. In this manner, both strands can be sequenced, which can provide greater accuracy for basecalling. The electrical signals for both strands can be compared as part of the basecalling.

In block 358, first electrical signals may then be detected as the first concatemer passes through the first nanopore. The first electrical signals may correspond to a first sequence of the first concatemer. The first electrical signals may include a current or a voltage. In the absence of a first concatemer passing through the first nanopore, an ionic current may pass between the electrodes. When a biomolecule, such as a concatemer, passes between the electrodes, the biomolecule may affect the passage of ions or electrons between the electrodes. The current or voltage, as a result, may decrease. The magnitude of the change may be related to the portion of the biomolecule between the electrodes. For example, the current or voltage may have a particular electrical signal signature when a specific nucleotide or functional group passes between the electrodes.

In some embodiments, the nanopore can be part of an electrical circuit that includes two electrodes. The current between the two electrodes can vary based on which nucleotide (base) or corresponding tag is in the nanopore. The first electrical signals can be detected using any suitable technique for measuring voltage or current in a circuit.

In block 360, method 350 may include analyzing the first electrical signals to determine the first sequence. The analysis can include comparing a pattern of electrical signals to known patterns that correspond to particular bases. Basecalling for nanopores may include using different models, including hidden Markov models, as discussed in Schreiber J. and Karplus K., "Analysis of nanopore data using hidden Markov models," Bioinformatics 2015 31:1897-1903, which is incorporated herein by reference for all purposes. Analyzing may include analyzing, by a computer system, the first electrical signals for the first strand and the second strand to determine the first sequence. For example, a sequence can be determined for the first strand and the second strand, and the two sequences can be compared to each other. The sequences should be complementary. Positions that are not complementary can, for example, be ignored or re-analyzed.

In some embodiments, the analysis of the first electrical signals may be used to determine a methylation classification for various sites of the first concatemer, e.g., CpG sites. The methylation classification may include whether a base is methylated, whether aberrant methylation (hypermethylation or hypomethylation) is present (e.g., whether a region, such as a CpG island has abnormal methylation), and whether the concatemer is hydroxyl methylated.

In block 362, method 350 may include aligning subsequences of the first sequence to identify fragment sequences corresponding to each of the first set of the DNA fragments. The subsequences can be any set of contiguous bases in the first sequence, e.g., as specified by sliding windows. An alignment can be performed to a reference genome, which can allow for mismatches in the alignment to the reference genome. The alignment of the subsequences is described in more detail below.

Concatemerizing can be performed for a second set of the DNA fragments to obtain a second concatemer, as well as for other sets of DNA fragments to obtain other concatemers. Each of the concatemers may have a different combination or permutation of DNA fragments than other concatemers. Each of the concatemers can be passed through the first nanopore or other nanopores of a plurality of nanopores that may comprise a sequencing device. Other electrical signals can be obtained as each of the other concatemers passes through a nanopore. The other electrical signals may correspond to a respective sequences of the other concatemers. Details involving the other concatemers may be similar to methods involving the first concatemer.

Method 350 may also include determining a size of each of the first set of the DNA fragments of the first concatemer. Sizes of DNA fragments of other sets of the DNA fragments of other concatemers can also be determined. As an example, the size of the DNA fragments may be determined by aligning subsequences with a reference genome or to known spacer sequences. For instance, if the spacer sequences can be identified, then the length of a DNA fragment can be identified as the number of bases between two spacer sequences. In such embodiments using a spacer sequence, the identified sequences of the DNA fragments need not be aligned to a reference genome to identify them, as the spacer sequences can provide such information. Further, the sequences of the DNA fragments can be assembled, after or instead of alignment to a reference genome. When aligning to the reference genome, determining the size of a DNA fragment may include determining the length of the longest subsequence that aligns to a single region of the reference genome.

3. Aligning Subsequences

Figure 4:
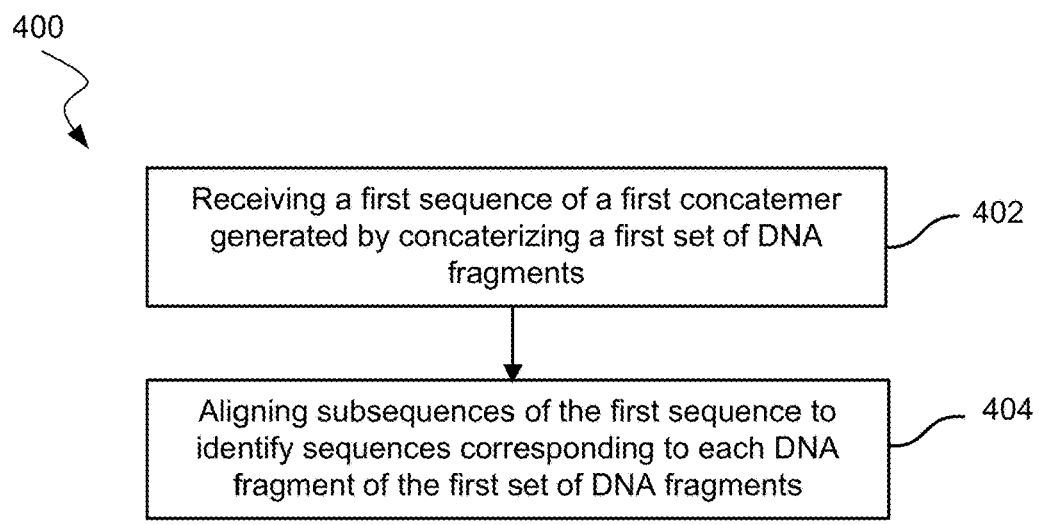
FIG. 4 shows a simplified block flow diagram of a method of analyzing a sequence of a concatemer according to embodiments of the present invention.

As shown in FIG. 4, embodiments may include a method 400 performed by a computer system. FIG. 4 shows a simplified block flow diagram of a method of analyzing a sequence of a concatemer according to embodiments of the present invention.

In block 402, method 400 may include receiving a first sequence of a first concatemer generated by concatemerizing a first set of DNA fragments. In some embodiments, the first concatemer may be generated by concatemerizing the first set of DNA fragments and a second set of DNA fragments. The first sequence may be received from a basecalling routine that may be resident on a sequencing device to which the computer system may also be resident. As another example, the computer system can be separate from the sequencing device and the first sequence can be received over a network connection or via a removable memory device. The concatemer may be any concatemer, e.g., as described herein.

In block 404, method 400 may also include aligning subsequences of the first sequence to identify fragment sequences corresponding to each DNA fragment of the first set of the DNA fragments. In some embodiments, aligning subsequences may include aligning subsequences to the second set of DNA fragments. The second set of DNA fragments may be a spacer DNA, as described herein. The spacer DNA may be a known sequence, which may be less than or equal to 20 nucleotides, including 15 to 20, 10 to 15, and 5 to 10 nucleotides.

In some embodiments, method 400 may include aligning subsequences of the first sequence to a reference genome. The reference genome may be the human genome. To identify the original units of plasma DNA molecules, embodiments can align the long DNA sequences to the human genome over windows. For example, a sliding window (e.g., 100-300 bases) can be selected from the long sequence of the concatemer, and the window sequence (subsequence) can be aligned to a reference genome. The reference genome may be a derivative of the reference human genome, e.g. but not limited to a subset of the human genome sequences, a repeat-masked genome, the exome, or part of the genome with moderate or balanced GC content.

The window can be moved (slid) forward or reverse by less of an amount than the length of the window (e.g., by 20-50 bases). The window in its new position may be considered a second window. The subsequence of this second window can also be aligned to the reference genome. If the subsequence of the second window is aligned to a subsequence of the reference genome that overlaps with a previous subsequence of the reference genome, then the two subsequences may be considered to be part of the same DNA fragment. If two sliding windows align to different, non-contiguous, or non-overlapping regions of the reference genome, then sequences of two DNA fragments may be distinguished.

If the subsequence does not align to the genome, but a subsequence before or after does, then an intersection (edge) between two DNA fragments can be identified. The regions to which the two DNA fragments aligned can be analyzed to determine the specific point of the intersection (e.g., the starting base of one DNA fragment and the ending base of the other DNA fragment). This intersection may be the ending or the beginning of a subsequence of a DNA fragment. This approach may be particularly useful when spacers are not used in the construction of concatemers. In other embodiments, specific sequences (e.g., specific barcodes or spacers) can be added to the end of the original molecules, and those specific sequences can indicate the ending of one molecule and the starting of another.

Accordingly, embodiments can find stretches or segments of DNA bases (generally up to hundreds of bases in length) that belonged to different regions on the human genome. Each contiguous stretch or segment of DNA bases may represent one original plasma DNA molecule. The adjacent juxtaposed stretches or segments of DNA that aligned to different distant parts of the human genome may belong to other plasma DNA molecules that got assembled into the concatemer.

The size of the window and the size of the step the window is moved or slid may be adjusted based on a desired resolution for the size of the DNA fragments. A smaller step size may increase the resolution of the determined size of the DNA fragments, while increasing computation intensity. A larger window size may not recognize DNA fragments smaller than the window size, while a smaller window size may not result in a unique alignment to the genome.

The window size and the step size may be dynamically adjusted. For example, a large step size may be used to narrow down areas of potential matches and then the step size may be decreased to more precisely identify the matches. Aligning the subsequence may be to a chromosome or a chromosomal region of the reference genome. Aligning the subsequence may include allowing a number of or frequency of mismatches to account for sequencing error. For example, aligning the sequence may allow for less than or equal to about 10-15% mismatches.

As discussed below, this approach was effective in sequencing plasma DNA molecules, identifying the human chromosomes, detecting the proportional differences between the nucleotide content of each chromosome and determining the size profile of the original plasma DNA sample before concatemerization. The concatemers may include DNA fragments from throughout the genome. The DNA fragments in the concatemer may be randomly distributed from all or almost all the chromosomes.

B. Increased Concentration

Another embodiment may include increasing the concentration of plasma DNA libraries loaded onto the sample chamber of the flow cell. Increasing the concentration of plasma DNA would not normally be expected to increase the efficiency of nanopore sequencing. Nanopores have relatively high sequencing errors, and given the small DNA fragment to analyze from plasma and other cell-free samples as well as the low DNA concentration in such cell-free samples, nanopores would not expected to effectively sequence the fragments. An increased concentration of DNA fragments would not be expected to address this issue. However, by concentrating the extracted DNA or input sequencing library, the chance of a DNA molecule reaching a nanopore or other single-molecule analysis technique is enhanced. Concentrating the extracted DNA involves concentrating beyond the level needed to obtain a volume compatible with a sequencing technique. In some cases, the concentration of the extracted DNA may increase by more than 10 fold. In other words, the volume may be reduced to less than 10% of the original.

Figure 5:
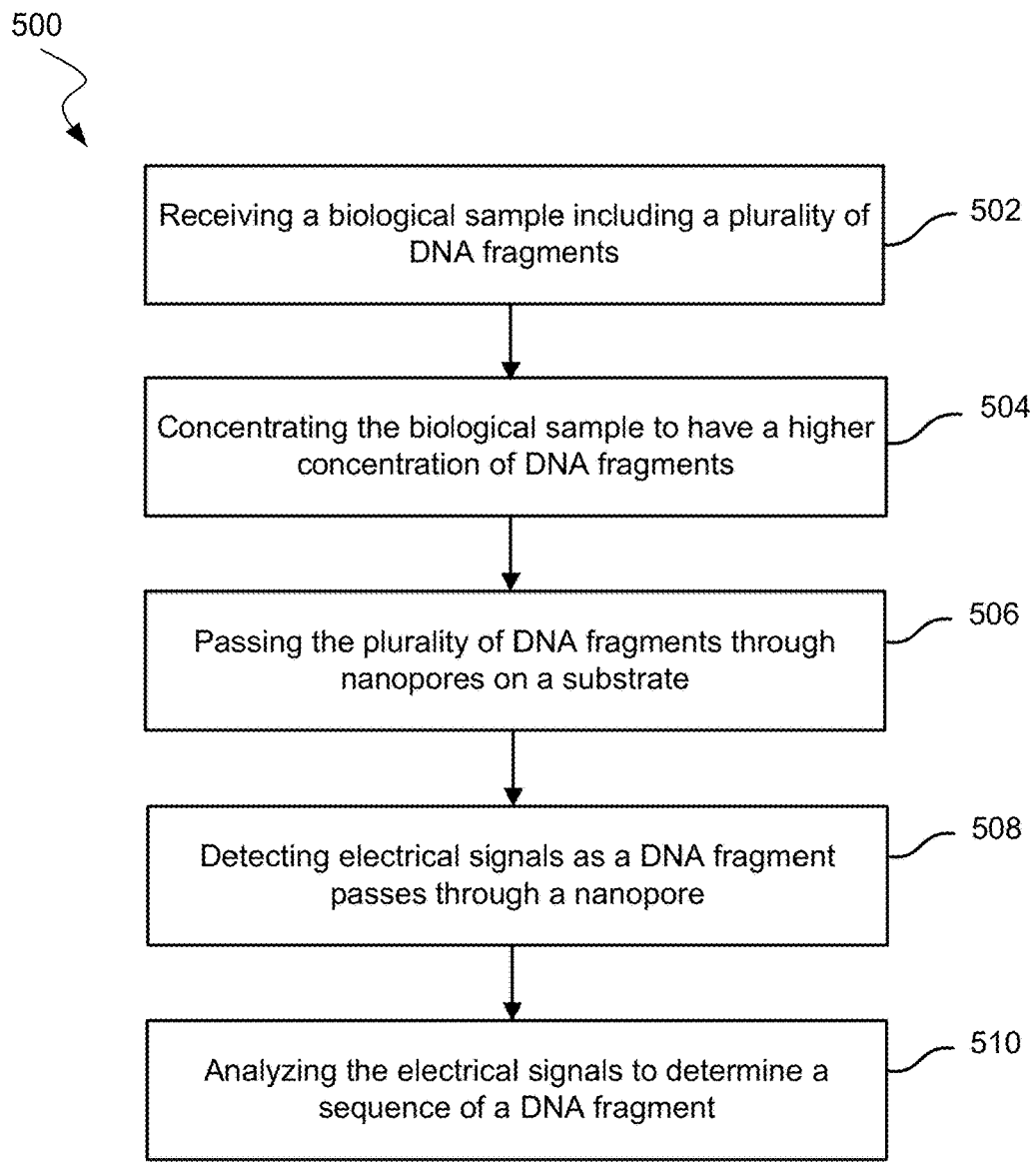
FIG. 5 shows a simplified block flow diagram of a method of more efficiently sequencing DNA fragments by increasing a concentration of DNA fragments multiple times according to embodiments of the present invention.

FIG. 5 shows a simplified block flow diagram of a method 500 of more efficiently sequencing DNA fragments by increasing a concentration of DNA fragments multiples times according to embodiments of the present invention. Method 500 can be used for various single-molecule sequencing platforms. In the example provided, a nanopore sequencing platform is described.

In block 502, method 500 may include receiving a biological sample including a plurality of DNA fragments. The biological sample may have a first concentration of DNA fragments in a starting volume. The biological sample may be of various types, e.g., as described herein. For example, the biological sample may be plasma or serum.

In block 504, method 500 may also include concentrating the biological sample to have a second concentration of DNA fragments. As various examples, the second concentration of DNA fragments may be 5 or more times, 6 or more times, 7 or more times, 8 or more times, 9 or more times, 10 or more times, 50 or more times, 100 or more times, 500 or more times, or 1000 or more times higher than the first concentration of DNA fragments. The concentration may be measured per volume or per mass.

The concentrating may be accomplished in various ways, as will be appreciated by one skilled in the art. For example, concentrating the biological sample may be by vacuum drying, by removing fluid by seepage or filtration, or by other concentrating techniques known to a person skilled in the art. Filtration or seepage may be combined with centrifugation and forcing the fluid through a size filter or molecular sieve. A semi-permeable membrane, which may permit a one-directional flow of fluid, may also be used in concentrating. The volume of the biological sample after concentrating may be reduced by an inverse proportion to the increase in concentration. For example, if the concentration is increased by a factor of 5, then the volume may be reduced by a factor of 5.

The concentration may increase significantly more than in conventional processes. In some conventional processes, a smaller volume of plasma DNA is extracted from a volume of plasma. In order to reduce the volume to meet reaction volume or other requirements in an analytical instrument, the volume may be concentrated further. For example, in a conventional process, 210 µL of plasma DNA may be extracted from 4 mL of plasma. The 210 µL of plasma DNA may be concentrated to 85 µL in order to provide a total reaction volume of 100 µL. With the conventional process, the increase in concentration is by less than a factor of 3, and the plasma DNA is not concentrated to improve sequencing accuracy or precision. In the present methods, the increased concentration may lead to more frequent passing of DNA fragments through nanopores or other sequencing devices and therefore improved detection and analysis.

In block 506, method 500 may further include passing the plurality of DNA fragments through nanpores on a substrate. In some embodiments, a method may include a single-molecule sequencing technique other than nanopores. For example, the sequencing technique may include the SMRT® technology by PACIFIC BIOSCIENCES® or Helicos sequencing by SEQLL®. Single-molecule sequencing techniques may include techniques described in Eid J. et al, "Real-time DNA sequencing from single polymerase molecules," Science 2009 323:133-138, the contents of which are incorporated herein by reference for all purposes.

In block 508, for each of the plurality of DNA fragments, electrical signals may be detected as the DNA fragment passes through a nanopore. The electrical signals may correspond to the sequence or a subsequence of the DNA fragment. The electrical signals may include a current or a voltage or any electrical signal described herein. When other sequencing techniques are used, fluorescent signals may be used instead of electrical signals.

In block 510, method 500 may include analyzing the electrical signals to determine the sequence or subsequence of the DNA fragment. Method 500 may include determining the size of the DNA fragment and the sizes of the plurality of DNA fragments, e.g., as by using alignment information. As a result, a size distribution of the DNA fragments may also be determined. Based on the size distribution of the DNA fragments, chromosomal differences may also be determined, e.g., as described in U.S. application Ser. No. 12/940,992, entitled "Size-based genomics," filed Nov. 5, 2010; U.S. application Ser. No. 13/308,473, entitled "Detection of genetic or molecular aberrations associated with cancer," filed Nov. 30, 2011; and U.S. application Ser. No. 13/789,553, entitled "Size-based analysis of fetal DNA fraction in maternal plasma," filed Mar. 7, 2013.

In some embodiments, the electrical signals may correspond to a methylation classification of the first concatemer. The methylation classification may include whether a base is methylated, whether aberrant methylation (hypermethylation or hypomethylation) is present, and whether the concatemer is hydroxyl methylated.

Methods may include aligning the sequences or subsequences of the DNA fragment with a reference genome. In particular, the alignment may be to a particular chromosome or chromosomal region of the reference genome.

The same DNA fragment may pass through the same nanopore multiple times. With each pass, the electrical signals may be detected. The electrical signals from different passes may be compared in order to aid in identifying the sequence. Increasing the concentration of DNA fragments may be used with single-molecule sequencing techniques other than nanopores.

III. EXAMPLES USING INCREASED CONCENTRATION

Examples show that plasma DNA may be concentrated to increase the efficiency of nanopore sequencing while providing accurate results. Sequencing using increased concentrations is further described in Cheng S. H. et al., "Noninvasive prenatal testing by nanopore sequencing of maternal plasma DNA: feasibility assessment," Clin. Chem. 61:10 (2015).

A. Materials and Methods

Plasma samples were obtained from four groups of individuals recruited with informed consent and institutional approval, namely, third-trimester pregnant women carrying male fetuses, third-trimester pregnant women carrying female fetuses, adult males and non-pregnant females. EDTA plasma samples were pooled within each group to provide at least 20 mL of plasma per group. The pooled plasma samples were extracted using a QIAAMP® DSP DNA blood mini kit (QIAGEN®, Germany) (2). The eluted plasma DNA with 1,050 µL per pool was concentrated by a SPEEDVAC® concentrator (THERMO FISHER SCIENTIFIC®, Waltham, Mass.) down to 85 µL. Each concentrated plasma DNA pool was fully consumed for the preparation of DNA libraries using end-repair and A-tailing modules (NEW ENGLAND BIOLABS®, Ipswich, Mass.), and a Genomic DNA Sequencing Kit (SQK-MAP-005, OXFORD NANOPORE TECHNOLOGIES®, UK). Each library (150 µL) was fully loaded onto a MINION® Flow Cell (v7.3) (Nanopore) and sequenced. The output data files were basecalled using the METRICHOR™ software (Nanopore). The 2D reads were extracted and aligned to the reference genome hg19 using LAST Genome-Scale Sequence Comparison software (Computational Biology Research Consortium, Japan).

The sequencing ran until each library was consumed and took 6 to 24 hours. 26.9%-32.5% of the reads passed the basecaller. The 2D read numbers were 56,844, 50,268, 35,878 and 36,167, for the plasma pools from pregnant women carrying male fetuses, those carrying female fetuses, adult males and non-pregnant females, respectively. The average observed identity, the proportion of bases in a read that align to a matching base in a reference sequence (3), was 82.7% (81.4-84.5%). Among the 2D reads, 16.9% (15.6-23.9%) were aligned to a unique genomic location and were further analyzed.

Figure 6:
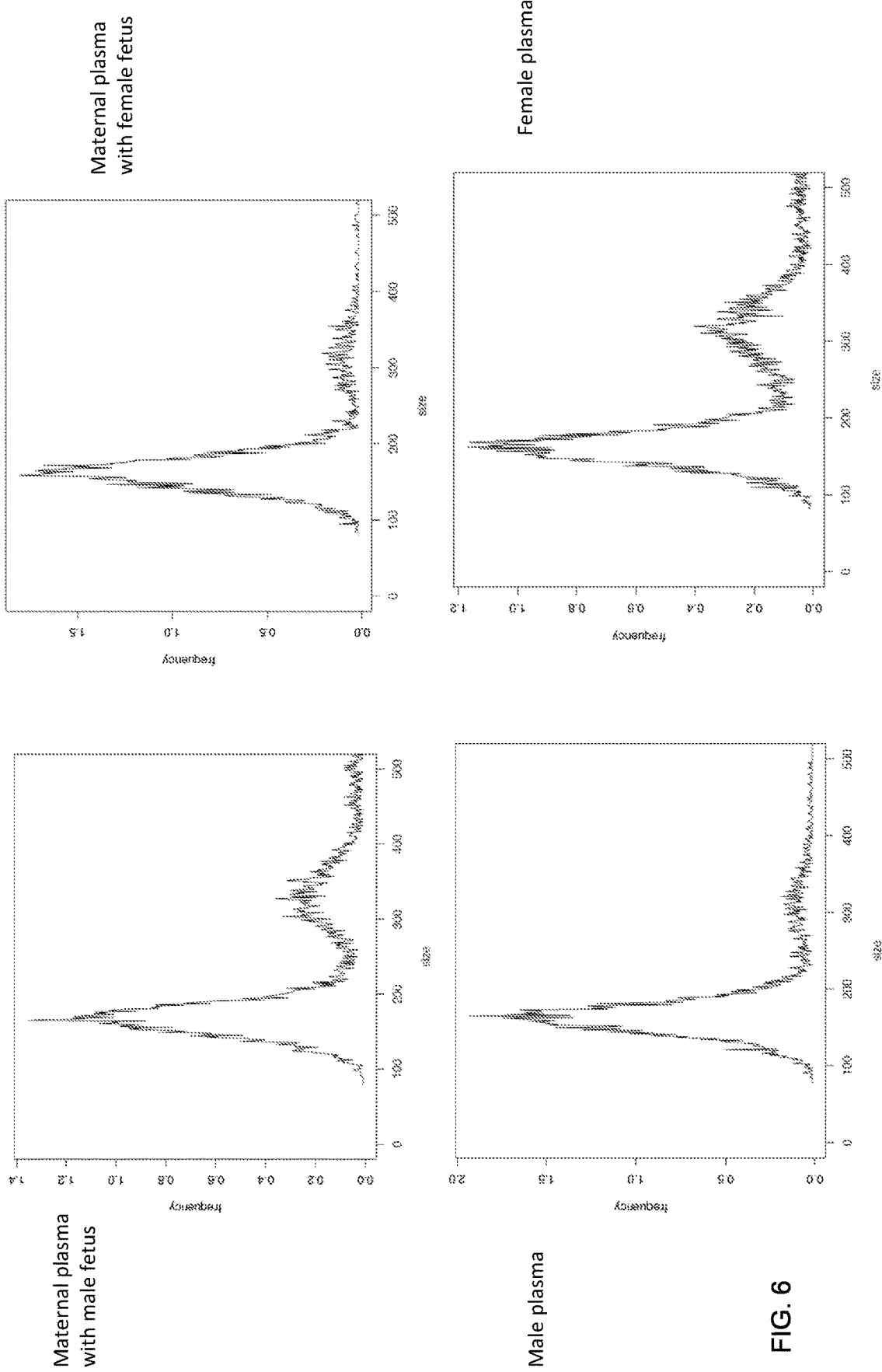
FIG. 6 shows size distributions of plasma DNA pools sequenced by the nanopore sequencer according to embodiments of the present invention. The frequency distribution of sequenced plasma DNA fragments ranging from 0 to 500 basepairs is plotted.

The sequenced plasma DNA fragments that aligned to the human genome ranged from 76 to 5,776 bp in length, and peaked at 162 bp (155-168 bp) (FIG. 6). Each of the graphs in FIG. 6 show the size of the sequenced plasma DNA fragments in base pairs on the x-axis, and the frequency of the plasma DNA fragment size as a percentage of the total plasma DNA fragments sequenced. The graphs are the results for DNA sequenced from maternal plasma with a male fetus, maternal plasma with a female fetus, male plasma, and non-pregnant female plasma. The peak plasma DNA sizes from the four plasmas are consistent with our previous findings based on Illumina's sequencing platforms (4). Minute quantities (0.06-0.3%) of long plasma DNA fragments (>1,000 bp) were observed from the nanopore sequencing data but not from previous data analyses on other sequencing platforms (4).

Figure 7:
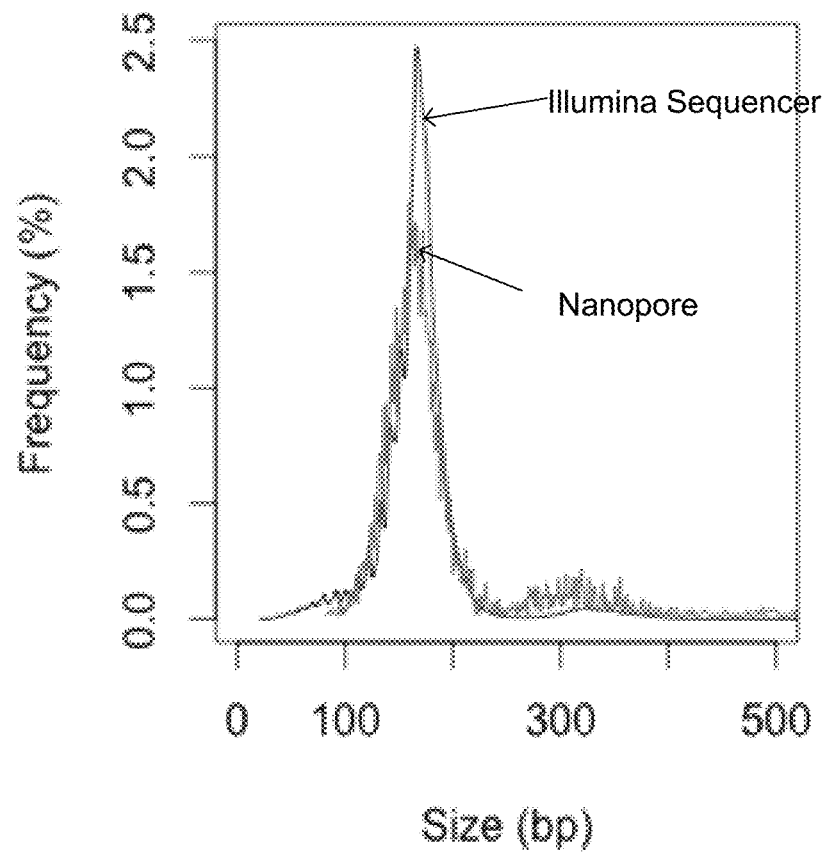
FIG. 7 shows the size profiles of plasma DNA from maternal plasma with a female fetus from data obtained by nanopore sequencing and with the Illumina sequencing platform according to embodiments of the present invention.

FIG. 7 shows the size profiles of plasma DNA from maternal plasma with a female fetus from data obtained by nanopore sequencing and obtained by the ILLUMINA® sequencing platform. The nanopore sequencing data are the same data as the maternal plasma with female fetus from FIG. 6. The size profiles in FIG. 7 have similar shapes with peaks at about the same sizes. For example, the size ratio of fragments less than or equal to 150 bp to fragments from 161 to 170 bp for nanopore sequencing is 1.21, compared to 1.10 for ILLUMINA® sequencing. These results showed that the size profile of plasma DNA can be accurately determined using a nanopore and concentrating plasma DNA. A peak in the 250-400 bp range is more prominent in data obtained by nanopore sequencing than by ILLUMINA® sequencing. This peak corresponds to cell-free DNA derived from dinucleosomes, and the presence of the peak varies across individuals. Additionally, the ILLUMINA® sequencing may be less efficient in sequencing fragments in this size range.

B. Analysis of Reads

Figure 8:
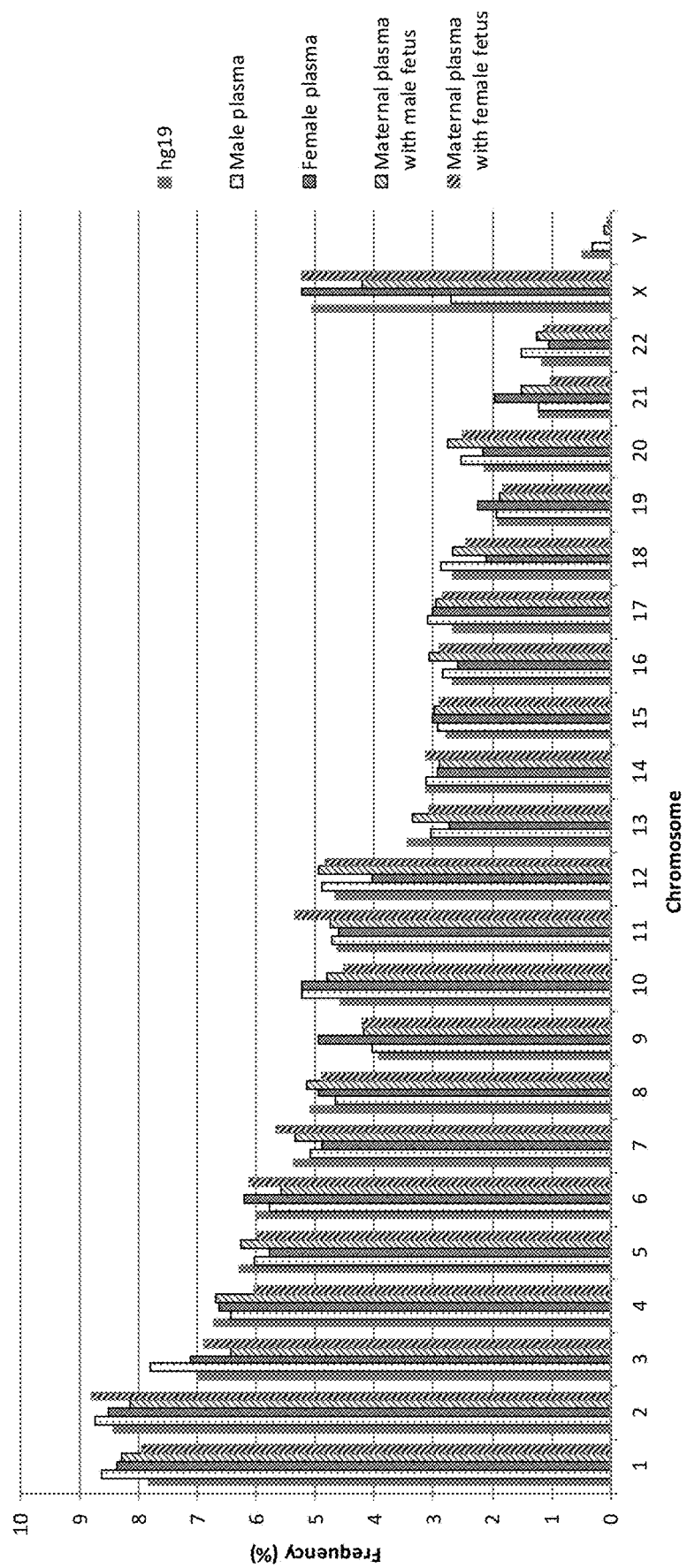
FIG. 8 shows the read distributions for chromosomes compared to a distribution expected from the mappable human genome according to embodiments of the present invention. Proportional distribution of nanopore sequence reads to each chromosome per sample pool. The filled grey bars represent the proportion of nucleotides originating from the respective human chromosomes based on the mappable part of the reference human genome, hg 19. The remaining colored bars represent the proportion of sequenced reads aligned to the respective human chromosomes for the plasma DNA samples.

FIG. 8 shows the read distributions for chromosomes compared to a distribution expected from the mappable human genome, labeled hg19. The chromosomes are listed on the x-axis. On the y-axis, the proportional distribution of reads to each chromosome (genomic representation) was calculated for each sample by counting the number of reads aligned to each chromosome over the total number of uniquely aligned reads sequenced from that sample and represented as a frequency and as a percentage. Plotted with hg19 are the results from maternal plasma with a male fetus, maternal plasma with a female fetus, male plasma, and non-pregnant female plasma. The read distributions to the autosomes for all four plasma DNA pools were comparable to those expected for the mappable human genome.

Differences in chromosome X and chromosome Y are observed in the read distribution. The proportion of reads mapped to chromosome X was lower in male plasma (2.70%) compared to female plasma (5.22%). Chromosome Y sequences were detected in the adult male (0.30%) plasma DNA pool but not in the non-pregnant female plasma DNA pool.

The plasma DNA pool from women pregnant with male fetuses had 0.11% of reads aligned to chromosome Y. Consistent with previous data (2), 0.018% of reads aligned to chromosome Y sequences in the plasma DNA pool from women pregnant with female fetuses. The presence of reads aligned to chromosome Y in women pregnant with female fetuses may be a result of a known error with aligning to a male genome. The maternal plasma DNA pool with male fetuses had around 1% less chromosome X sequences than those women pregnant with female fetuses.

The relative distribution of reads for chromosome X and chromosome Y are observed to be similar to the expected outcome. Male plasma showed more chromosome Y than plasma from both pregnant and non-pregnant females. Male plasma had less chromosome X than plasma from both pregnant and non-pregnant females. Male plasma had about half the amount of chromosome X as the non-pregnant female, which is expected because males have only one chromosome X while females have two chromosome X. Maternal plasma with a male fetus had a higher read distribution of chromosome Y than maternal plasma with a female fetus and female plasma.

Thus, fetal DNA sequences and chromosome X dosage differences between male and female fetuses are detectable by nanopore sequencing and concentrating plasma DNA. The chromosome X dosage of a male fetus is equivalent to the chromosome X dosage of a female fetus with monosomy X or Turner syndrome. Thus, this observation suggests the potential feasibility of using nanopore sequencing for the noninvasive detection of fetal chromosomal aneuploidies, such as monosomy X, or copy number aberrations. Since monosomy X represents the reduction of one chromosome copy in the genome, the extent of copy number change is equivalent to a trisomy where there is an addition of one chromosome copy in the genome. Hence, these data also reflect that our protocol could be applied to the non-invasive detection of fetal trisomy 21, trisomy 18, trisomy 13 and other fetal chromosomal aneuploidies. These data suggest the feasibility of nanopore sequencing-based NIPT and point-of-care NIPT.

IV. CANCER SEQUENCING USING INCREASED CONCENTRATION

Circulating cell-free DNA may be used as a "liquid biopsy" for real-time monitoring of cancers. Cell-free DNA exhibits genetic anomalies found in the underlying tumors, which can be detected by massively parallel sequencing technology. These chromosomal aberrations in plasma DNA of cancer patients may also be detected using nanopore sequencing. Plasma DNA samples from two patients with hepatocellular carcinoma (HCC) were analyzed by both nanopore sequencing and massively parallel sequencing on Illumina's platform.

A. Materials and Methods

Twenty milliliters each of peripheral blood was collected from two patients diagnosed with HCC before operation. Plasma was isolated by centrifugation at 1600×g for 10 minutes, then at 16000×g for 10 minutes. DNA was extracted from 8 mL of plasma using a QIAAMP® DSP DNA blood mini kit (QIAGEN®). Three-quarters of plasma DNA was subjected to nanopore sequencing, while the remaining DNA was sequenced by NEXTSEQ® 500 (ILLUMINA®).

Nanopore sequencing libraries were prepared by end-repair/dA-tailing module (NEB), and a Nanopore Sequencing Kit (SQK-NSK007, OXFORD NANOPORE TECHNOLOGIES®). The library was fully loaded onto a MINION® Flow Cell (R9 version) and sequenced on a MINION® Mk1B sequencer (Nanopore). The output data files were basecalled using the METRICHOR™ software (Nanopore). The 2D reads were extracted and aligned to the reference genome hg19 using LAST software. The ILLUMINA® sequencing of the plasma DNA was performed as previously described (8).

B. Results

The proportional distribution of the aligned reads to each chromosome arm (genomic representation, GR) was calculated for each sample. In other words, the number of high quality passed-filter reads that aligned to a chromosome arm, p or q arm, was expressed as a proportion of all high quality passed-filter reads sequenced from the sample. The difference in GR relative to plasma DNA samples of normal individuals was then calculated. If the GR of a chromosome arm is 3 standard deviations above the mean of the control group, the region is considered to demonstrate a copy number gain. If the GR of a chromosome arm is 3 standard deviations below the mean of the control group, the region is considered to demonstrate a copy number loss.

Figure 9:
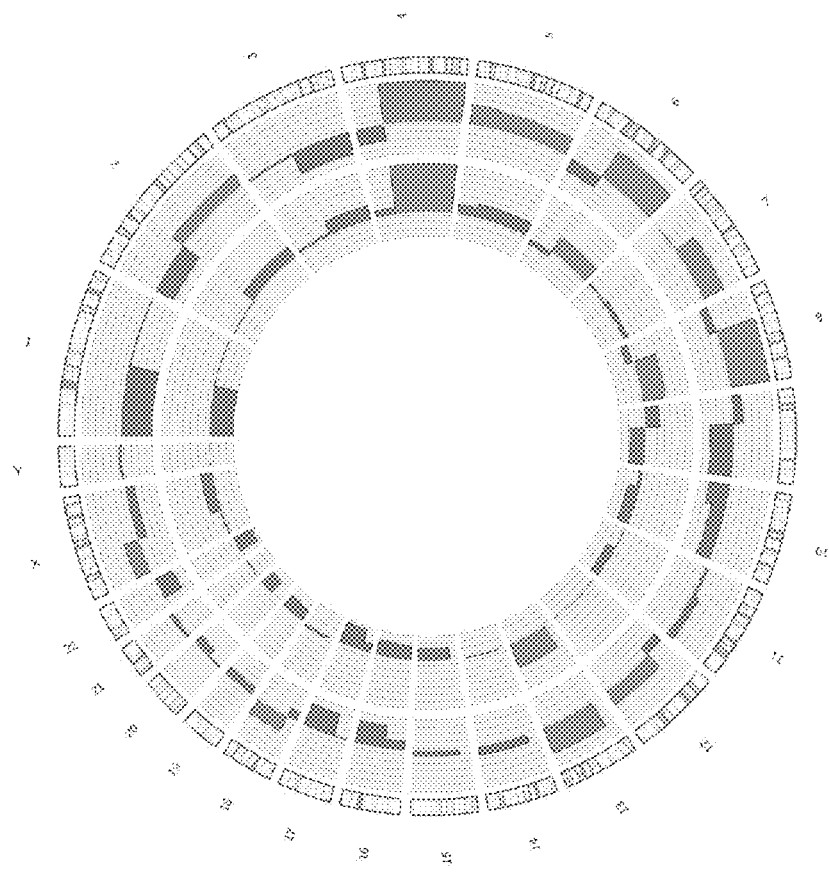
FIG. 9 shows a Circos plot of the results of sequencing plasma DNA from cancer patients using nanopore sequencing and massively parallel sequencing according to embodiments of the present invention.
Figure 9:
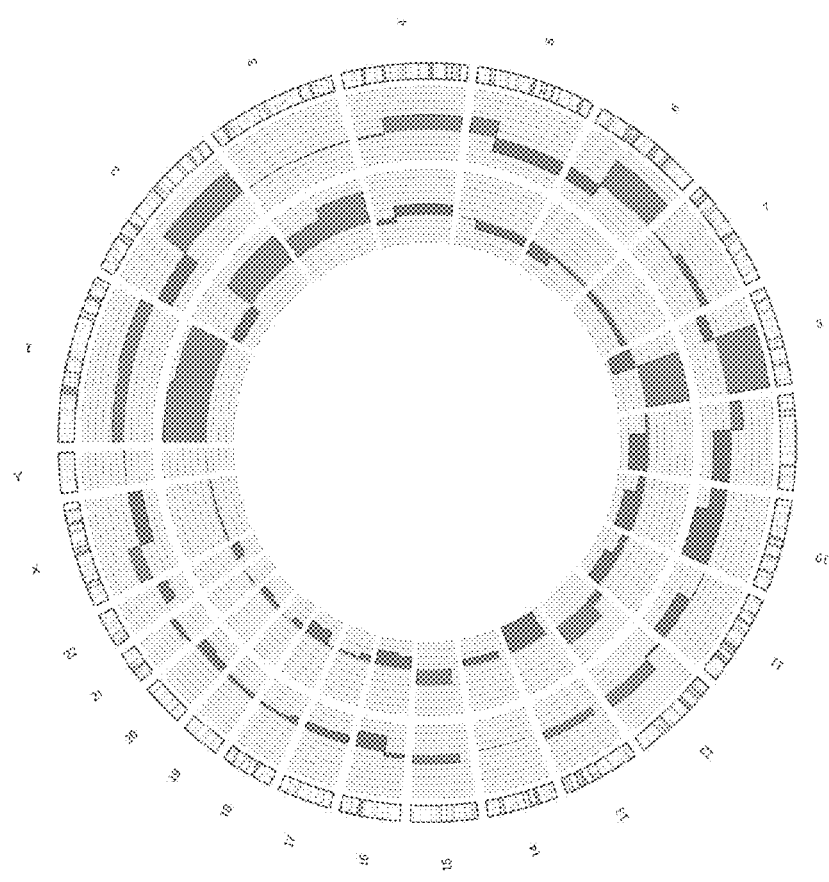

FIG. 9 shows the difference in GR on two cases (HOT530 and HOT536) of HCC by nanopore sequencing (outer ring) and by Illumina's platform (inner ring). The difference chromosomes are labeled on the outside. The analyzed regions were the arms of the chromosomes. Chromosomal gains are represented as green bars and as extending outward from the center of the respective ring. Chromosomal losses are represented as red bars and as extending inward from the center of the respective ring. As seen in FIG. 9, the results from nanopore sequencing were largely concordant to the results generated by Illumina's platform. The sequenced samples also showed a trend of having longer DNA as compared to plasma DNA from non-cancer subjects. This example shows that nanopore sequencing with the increased concentration method may be used for analysis of plasma DNA from cancer patients.

V. EXAMPLES USING CONCATEMERS

Plasma DNA molecules are typically short (<200 bp), and nanopore sequencers may typically be used to sequence long DNA molecules. The efficiency of sequencing the short plasma DNA molecules could be improved by linking or joining individual molecules to construct long DNA molecules, termed concatemers.

A. Materials and Methods

1. Generation of Plasma DNA Concatemers

Samples from two different subjects were tested. Twenty milliliters of peripheral venous blood was collected from both a non-pregnant female subject and a female subject pregnant with a male fetus. Plasma was harvested after centrifugation at 1600×g for 10 minutes and further centrifuged at 16000×g for 10 minutes. DNA was then extracted from 8 mL of plasma using a QIAAMP® DSP DNA blood mini kit (QIAGEN®), resulting in a volume of 420 μl of plasma DNA. The extracted DNA was concentrated to 85 μL by a SPEEDVAC® concentrator (THERMO FISHER SCIENTIFIC®) and was end-repaired by a NEBNEXT® End-Repair module (NEW ENGLAND BIOLABS®, NEB®). The end-repaired DNA was purified using MINELUTE® Reaction Cleanup Kit (QIAGEN®) and eluted with 20 μL buffer EB. Next, the plasma DNA was concatenated by adding 20 μL Blunt/TA Ligase Master Mix (NEB®) with incubation at 25° C. for 4 hours, and purified with MINELUTE® Reaction Cleanup kit after the incubation.

2. Nanopore Sequencing

The concatenated DNA was then used for nanopore sequencing library preparation by end-repair and A-tailing modules (NEB®), and a Genomic DNA Sequencing Kit (SQK-MAP-005, OXFORD NANOPORE TECHNOLOGIES®). The library was fully loaded onto a MINION® Flow Cell (v7.3) (Nanopore) and sequenced. The output data files were basecalled using the METRICHOR™ software (Nanopore). The 2D reads were extracted.

3. Alignment

Alignment was performed using LAST software. Initial matches were found for each possible start position. The matches were limited to matches with a minimum length that occur a maximum number of times in the reference genome, or the matches were limited to a specific predetermined length. From these initial matches, additional alignments for sequences longer than these initial matches were performed and ones that had a certain gap score were retained based on desired tolerance for sequencing errors. If multiple alignments shared the same endpoint, the alignment with the highest score was retained. In this manner, fragments aligned to the human genome were identified. Parameters and rules used in LAST may be changed depending on accuracy and precision considerations.

B. Results

The concatenated plasma DNA was sequenced on the MINION® for 6 hours until the library was consumed.

1. Non-Pregnant Female

Figure 10:
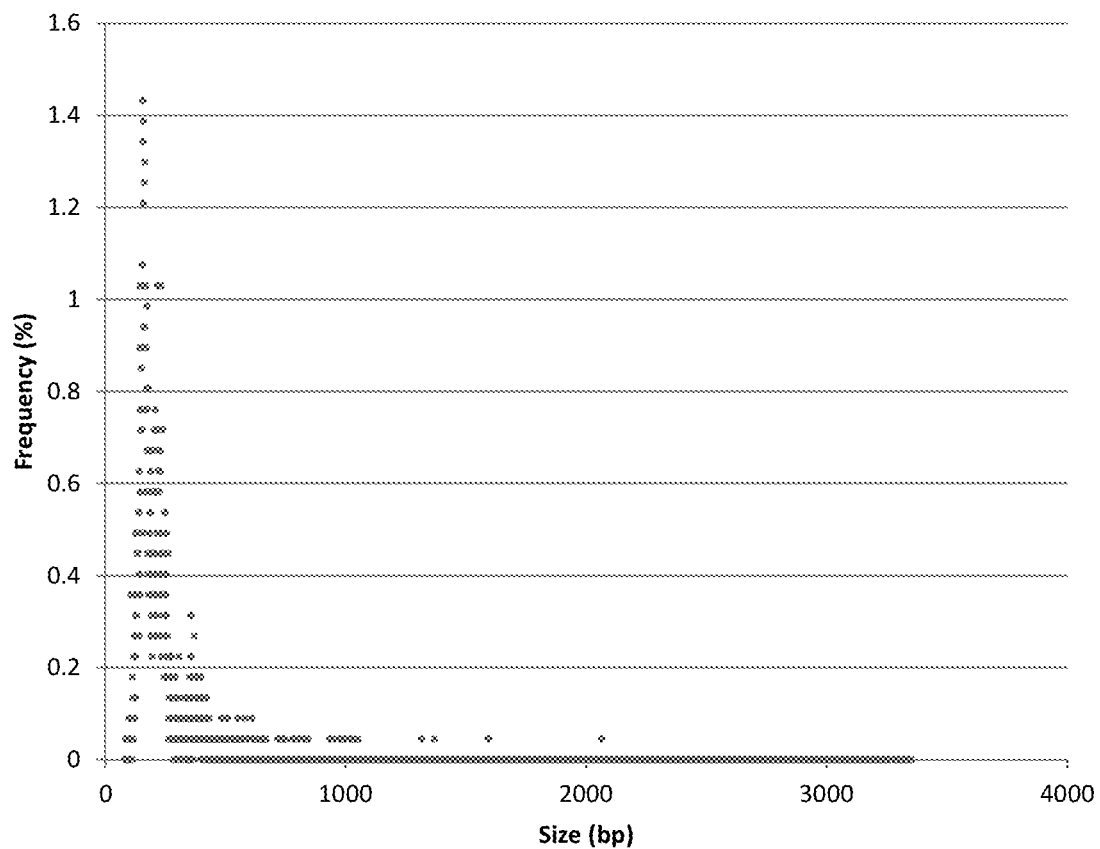
FIG. 10 shows a size distribution of the concatemerized DNA molecules according to embodiments of the present invention.

The basecalling yielded 2,234 2D reads, with the read length ranged from 86 to 8,672 bp. FIG. 10 shows a frequency distribution curve of the sizes of concatemers that were sequenced from the non-pregnant female. The size of a concatemer in base pairs is on the x-axis. The frequency, represented as a percentage, that a given concatemer size is present in the sequenced sample is plotted on the y-axis. An outlier data point at 8,672 bp outlier data point is not shown in order to improve graph readability. For each sequenced sample, about 20 to 50 long DNA molecules were detected.

The sizes of the sequenced molecules were much longer than the typical length of plasma DNA fragments, which are generally less than 200 bp. These data indicate that the plasma DNA fragments had been assembled as concatemers successfully. The reads were then aligned to the human genome (hg19). Stretches of bases, or segments, that belonged to disjointed regions on the human genome were then separated and considered as one plasma DNA fragment. In total, 3,801 uniquely mapped segments, namely sequenced plasma DNA fragments, were obtained, and 80.6% of the uniquely mapped segments showed identical sequence to the reference genome.

Figure 11:
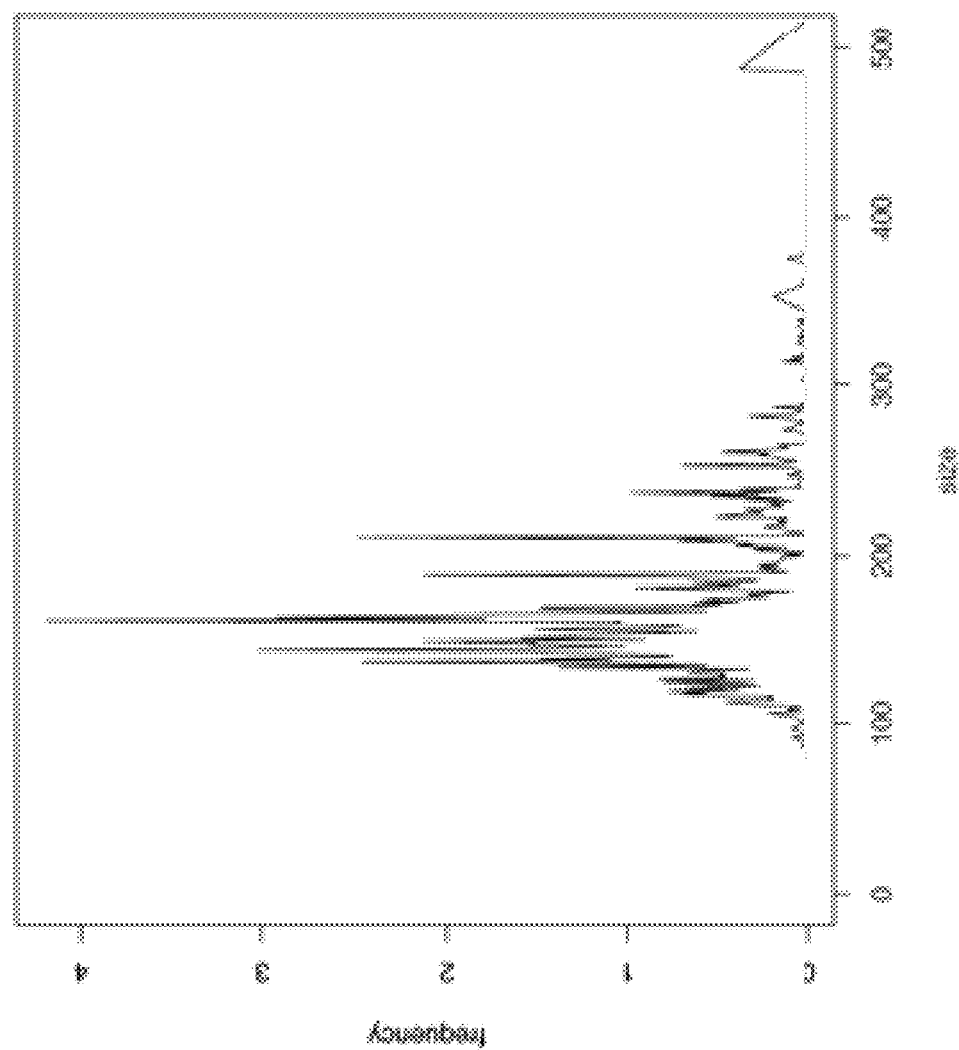
FIG. 11 shows a size distribution of the plasma DNA molecules derived from the concatemerized segments from a non-pregnant female according to embodiments of the present invention.

FIG. 11 shows the size distribution of the aligned segments of the non-pregnant female. The sizes of these aligned segments varied from 78 to 560 bp, with most below 200 bp. The peak size was 162 bp. The mean size was 173 bp. The median size was 162 bp, which is consistent with previous observations on the size of plasma DNA by massively parallel sequencing on the ILLUMINA® platform and also by nanopore sequencing using an increased concentration of DNA fragments.

Figure 12:
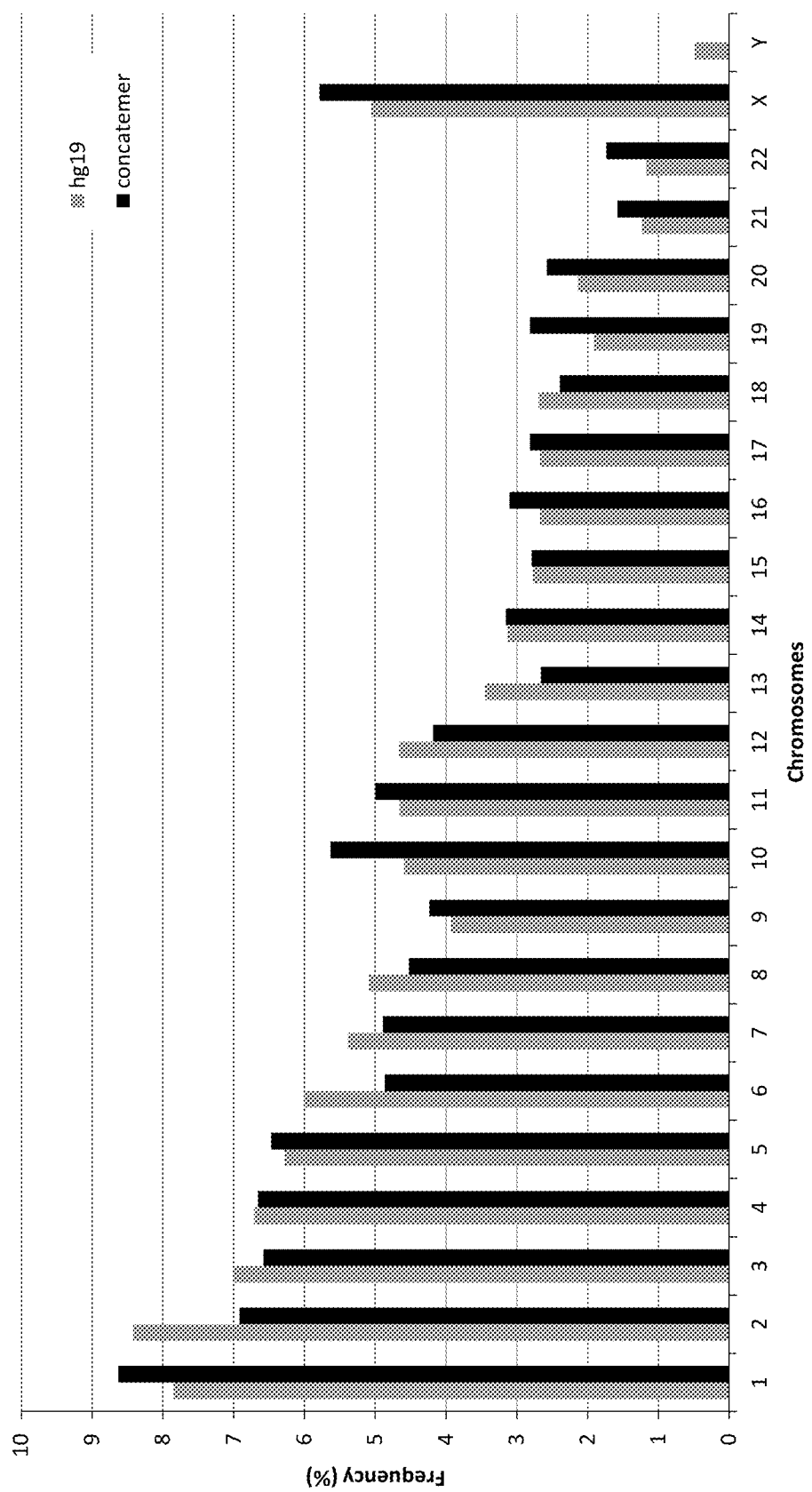
FIG. 12 shows a genomic representation of aligned segments from concatenated plasma DNA from a non-pregnant female according to embodiments of the present invention.

FIG. 12 shows the computed distribution of the aligned segments compared to a reference genome from a male. The proportional distribution of the aligned segments to each chromosome (genomic representation) were computed. The computed distribution was similar to the distribution of hg19 among all autosomes. For sex chromosomes, the genomic representation of chromosome X was 5.79%, which is anticipated for a female sample. No misalignment to chromosome Y was found. Thus, methods of using a concatemer with a nanopore may distinguish female plasma from male plasma.

2. Female Pregnant with Male Fetus

The male fetus in the pregnant female had a gestational age of 38 weeks and 4 days when a blood sample was taken. The pregnancy was considered normal. The plasma DNA fragments were concatemerized before processing for nanopore sequencing. The size of the concatemers ranged from 100 to 13,466 bp, with a median size of 676 bp and a mean size of 965 bp.

Figure 13:
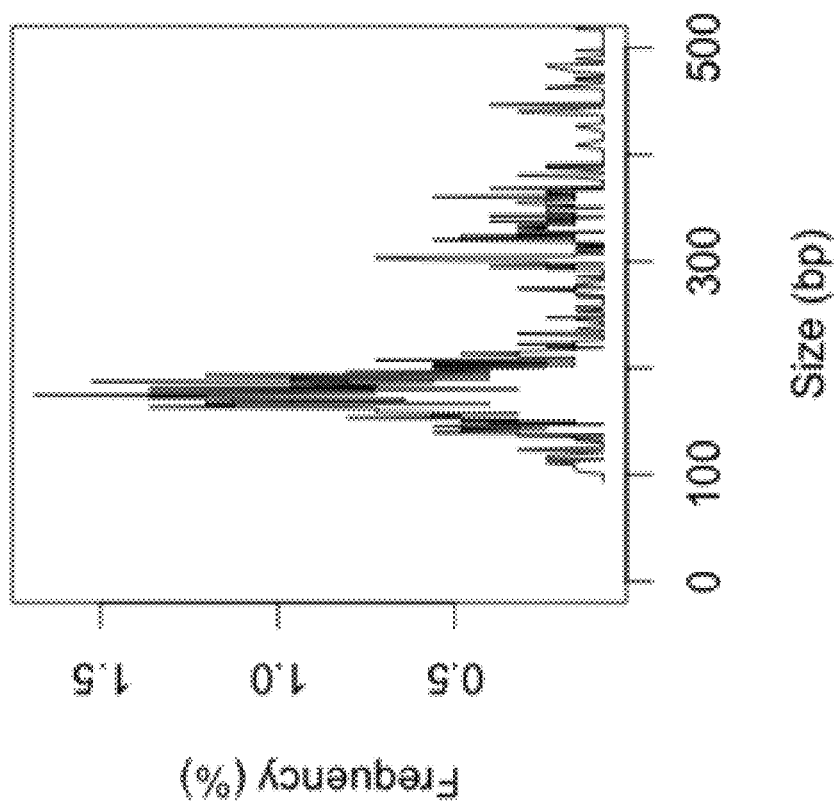
FIG. 13 shows a size distribution of the plasma DNA molecules derived from the concatemerized segments from a female pregnant with a male fetus according to embodiments of the present invention.

FIG. 13 shows the size profile of the aligned segments of the concatemer for the female pregnant with a male fetus. The size profile is typical of plasma DNA. The median size of the fragments was 196 bp. The peak size was 174 bp, with the size ranging from 92 to 2,934 bp. Only about 0.4% of the fragments had a size greater than 2,000 bp. This distribution is similar to the other size distributions obtained by methods using concatemers, increased concentration, or massively parallel sequencing. For example, the distribution is similar to size distribution found using the increased concentration method for maternal plasma with a male fetus, as shown in FIG. 6.

Figure 14:
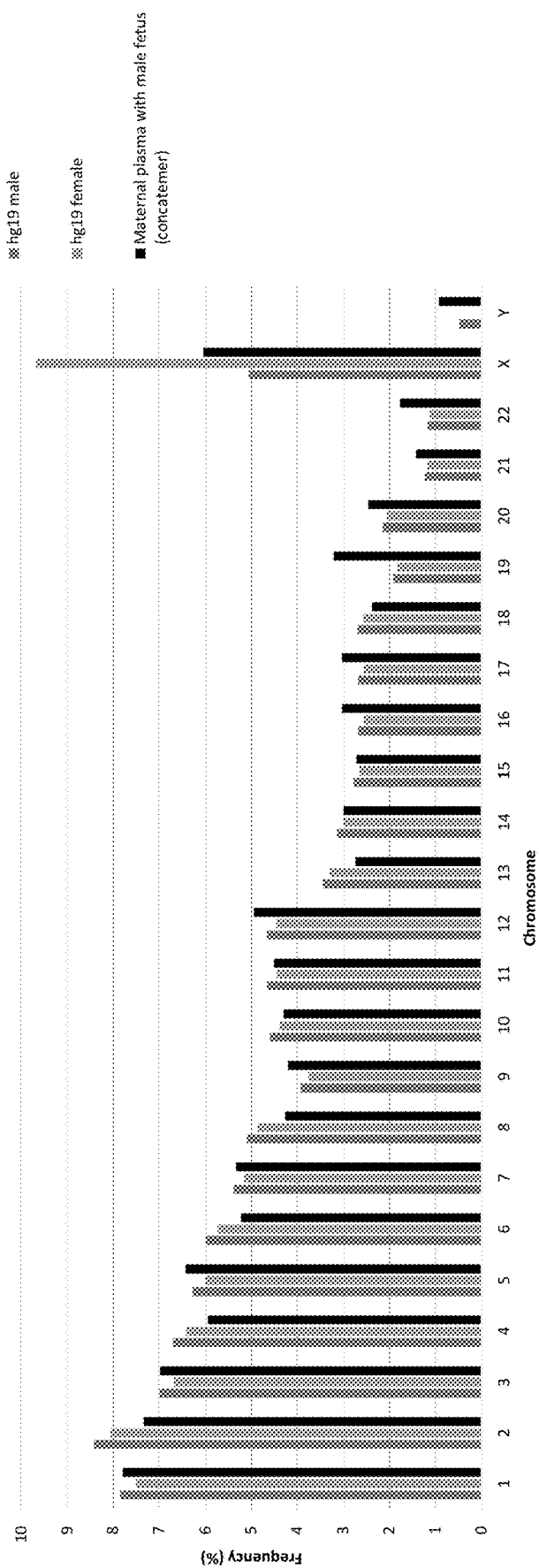
FIG. 14 shows a genomic representation of aligned segments from concatenated plasma DNA from a female pregnant with a male fetus according to embodiments of the present invention.

FIG. 14 shows the computed chromosomal distribution of the aligned segments for the female pregnant with a male fetus compared to reference genomes for a male and a non-pregnant female. The distribution of the concatemers show a chromosomal X level between that of the male and non-pregnant female levels. This suggests that the chromosome X data are reflecting the monosomy of chromosome X of the normal male fetus. In addition, the concatemer shows evidence of the fetal-derived chromosome Y. Some deviations of the read distribution obtained by sequencing from the reference genome may be a result of limiting analysis to only alignable portions of the reference genome. Nevertheless, as shown by these results, methods of using a concatemer may distinguish a maternal plasma with a male fetus from a male or non-pregnant female. These methods likely could be used to distinguish a maternal plasma with a male fetus from a maternal plasma with a female fetus.

VI. FURTHER EMBODIMENTS

Embodiment 1 includes a method comprising: receiving a plurality of DNA fragments; concatemerizing a first set of the DNA fragments to obtain a first concatemer; passing the first concatemer through a first nanopore; and detecting first electrical signal as the first concatemer passes through the first nanopore, the electrical signals corresponding to a first sequence of the first concatemer.

Embodiment 2 includes the method of embodiment 1, further comprising performing by a computer system: analyzing the first electrical signals to determine the first sequence; and aligning subsequences of the first sequence to a reference genome to identify fragment sequences corresponding to each of the first set of the DNA fragments.

Embodiment 3 include the method of embodiment 1, wherein passing the first concatemer through a first nanopore includes: passing a first strand of the first concatemer through the nanopore; and subsequently, passing a second strand of the first concatemer through the nanopore. Embodiment 4 includes the method of embodiment 3, further comprising analyzing, by a computer system, the first electrical signals for the first strand and the second strand to determine the first sequence.

Embodiment 5 includes the method of embodiment 1, wherein the plurality of DNA fragments are cell-free DNA fragments from a biological sample.

Embodiment 6 includes the method of embodiment 2, wherein the biological sample is plasma or serum.

Embodiment 7 includes the method of embodiment 1, wherein the first nanopore is one of a plurality of nanopores on a substrate. Embodiment 8 includes the method of embodiment 7, further comprising: concatemerizing a second set of the DNA fragments to obtain a second concatemer; passing the second concatemer through a second nanopore of the plurality of nanopores; and detecting electrical signal as the second concatemer passes through the second nanopore, the electrical signals corresponding to a second sequence of the second concatemer. Embodiment 9 includes the method of embodiment 7, further comprising: concatemerizing a second set of the DNA fragments to obtain a second concatemer; passing the second concatemer through the first nanopore; and detecting electrical signal as the second concatemer passes through the first nanopore, the electrical signals corresponding to a second sequence of the second concatemer.

Embodiment 10 include a method comprising: receiving a biological sample including a plurality of DNA fragments; concentrating the biological sample to have a higher concentration of DNA fragments; passing the plurality of DNA fragments through nanopores on a substrate; and for each of the plurality of DNA fragments: detecting electrical signals as the DNA fragment passes through a nanopore, the electrical signals corresponding to the sequence of the DNA fragment.

Embodiment 11 includes a method comprising performing by a computer system: receiving a first sequence of a first concatemer generated by concatemerizing a first set of DNA fragments; and aligning subsequences of the first sequence to a reference genome to identify fragment sequences corresponding to each of the first set of the DNA fragments. Embodiment 12 includes the method of embodiment 11, wherein the aligning of the subsequences includes: aligning windows of the first sequence to the reference genome; and identifying when two windows align to different regions of the reference genome. Embodiment 13 includes the method of embodiment 12, wherein one or more windows between the two windows are identified as not aligning to the reference genome.

Embodiment 14 includes a computer product comprising a computer readable medium storing a plurality of instructions for controlling a computer system to perform an operation of any one of embodiments 11-13. Embodiment 15 includes a system comprising: the computer product of embodiment 14; and one or more processors for executing instructions stored on the computer readable medium. Embodiment 16 includes a system comprising means for performing of any one of embodiments 11-13. Embodiment 17 includes a system configured to perform of any one of embodiments 11-13. Embodiment 18 includes a system comprising modules that respectively perform the steps of of any one of embodiments 11-13.

VII. EXAMPLE SEQUENCING SYSTEM

Figure 15:
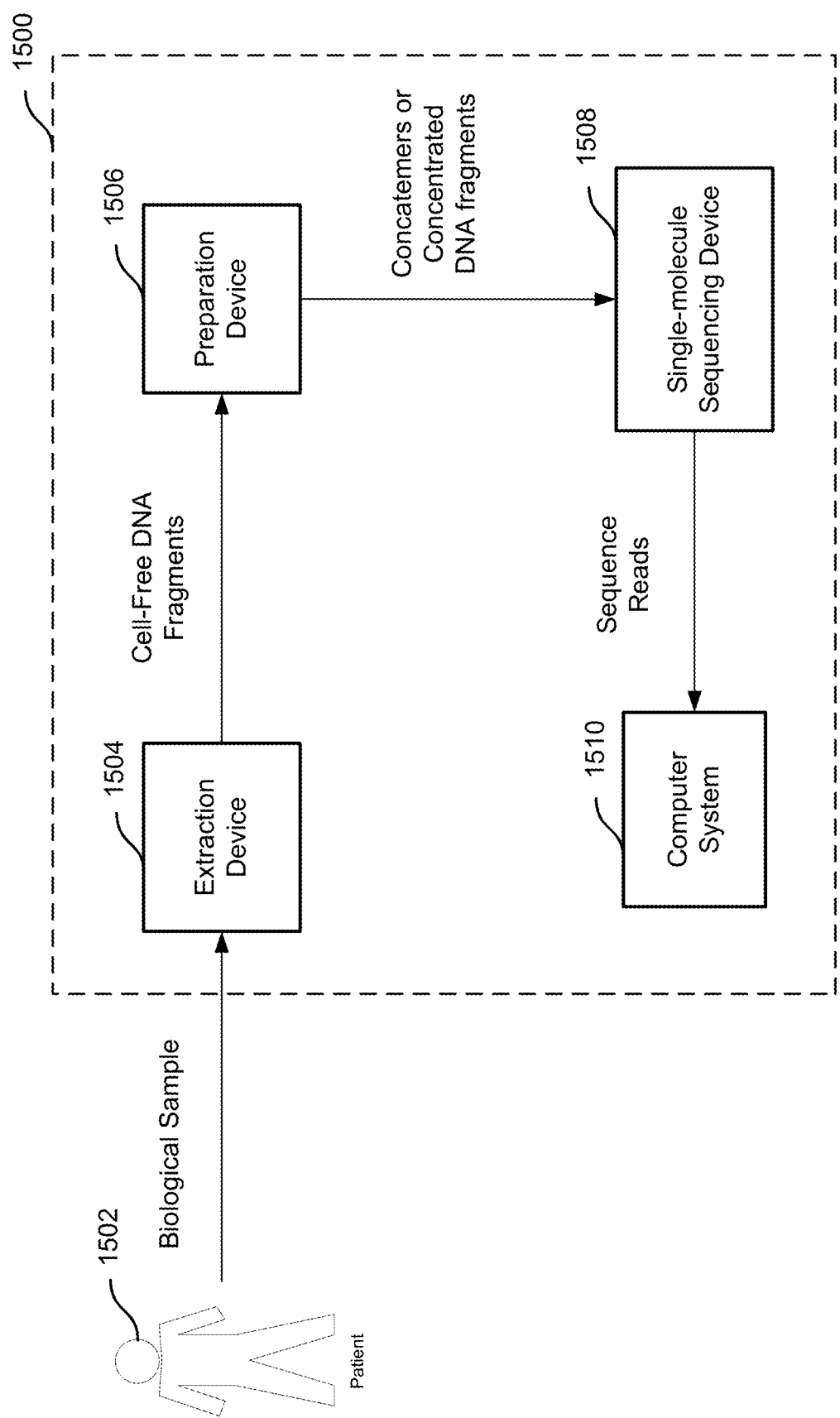
FIG. 15 shows a block diagram of a system for performing according to embodiments of the present invention.

FIG. 15 shows a block diagram of a system 1500 for performing single-molecule sequencing according to embodiments of the present invention. A biological sample may be obtained from a patient 1502 by an extraction device 1504. The biological sample may be any bodily fluid or any biological sample described herein. Extraction device 1504 may include a syringe, a lancet, a swab, or a container or vial for collecting a sample such as urine. Extraction device 1504 may include a QIAAMP® DNA blood mini kit (QIAGEN®, Germany) (2). The biological sample may contain cell-free DNA fragments, which are sent to a preparation device 1506. Preparation device 1506 may include a device that produces a form of the cell-free DNA fragments that is more efficient for single-molecule sequencing. For example, the output of preparation device 1506 may be concatemers or a concentrated sample of the cell-free DNA fragments.

When concatemers are produced, preparation device 1506 may include a vacuum dryer to increase the concentration, such as a SPEEDVAC® concentrator (THERMO FISHER SCIENTIFIC®) or an ultraconcentrator that removes fluid by seepage or filtration. For concatemers, the concentration may not be increased by a factor of five or more. Preparation device 1506 may include a module to repair ends of DNA fragments, such as NEBNEXT® End-Repair module (New England Biolabs, NEB). In addition, preparation device 1506 may include a kit to purify the end-repaired DNA, such as a MINELUTE® Reaction Cleanup Kit)(QIAGEN®. Preparation device 1506 may also include an incubator that may incubate ligase enzymes (e.g., Blunt/TA Ligase Master Mix)) (NEB®)) at a temperature for several hours (e.g., 25° C. for 4 hours). Preparation device 1506 may include an additional kit to purify the concatemers after reaction, which may include the MINELUTE® Reaction Cleanup Kit)(QIAGEN®. Preparation device 1506 may also include a robotic liquid handler, which may mix and transfer fluids.

When an increased concentration of cell-free DNA fragments is produced, preparation device 1506 may include a vacuum dryer (e.g., a SPEEDVAC® concentrator (THERMO FISHER SCIENTIFIC®, Waltham, Mass.)) or an ultraconcentrator that removes fluid by seepage or filtration. Preparation device 1506 may also include end-repair and A-tailing modules (NEW ENGLAND BIOLABS®, Ipswich, Mass.). Preparation device 1506 may also include a robotic liquid handler, which may mix and transfer fluids.

The concatemers or the concentrated DNA fragments from preparation device 1506 may be sent to a single-molecule sequencing device 1508 to obtain sequence reads. Single-molecule sequencing device 1508 may also include a device such as MINION® Flow Cell (v7.3) (Nanopore), SMRT® technology (PACIFIC BIOSCIENCES®), or Helicos Single Molecule sequencers)(SEQLL®). Single-molecule sequencing device 1508 may also include kits associated with a nanopore, such as Genomic DNA Sequencing Kit (SQK-MAP-005, OXFORD NANOPORE TECHNOLOGIES®, UK) or Nanopore Sequencing Kit (SQK-NSK007, OXFORD NANOPORE TECHNOLOGIES®).

Single-molecule sequencing device 1508 may output sequence reads from the concatemers or concentrated DNA fragments. The sequence reads may be outputted as data files and may be analyzed by a computer system 1510. The computer system may be a specialized computer system with software to analyze the sequence reads. The output data files may be basecalled using the METRICHOR™ software (Nanopore). The 2D reads may be extracted and aligned using LAST software. The computer system may be the computer system 10 in FIG. 16, as described below.

VIII. COMPUTER SYSTEM

Figure 16:
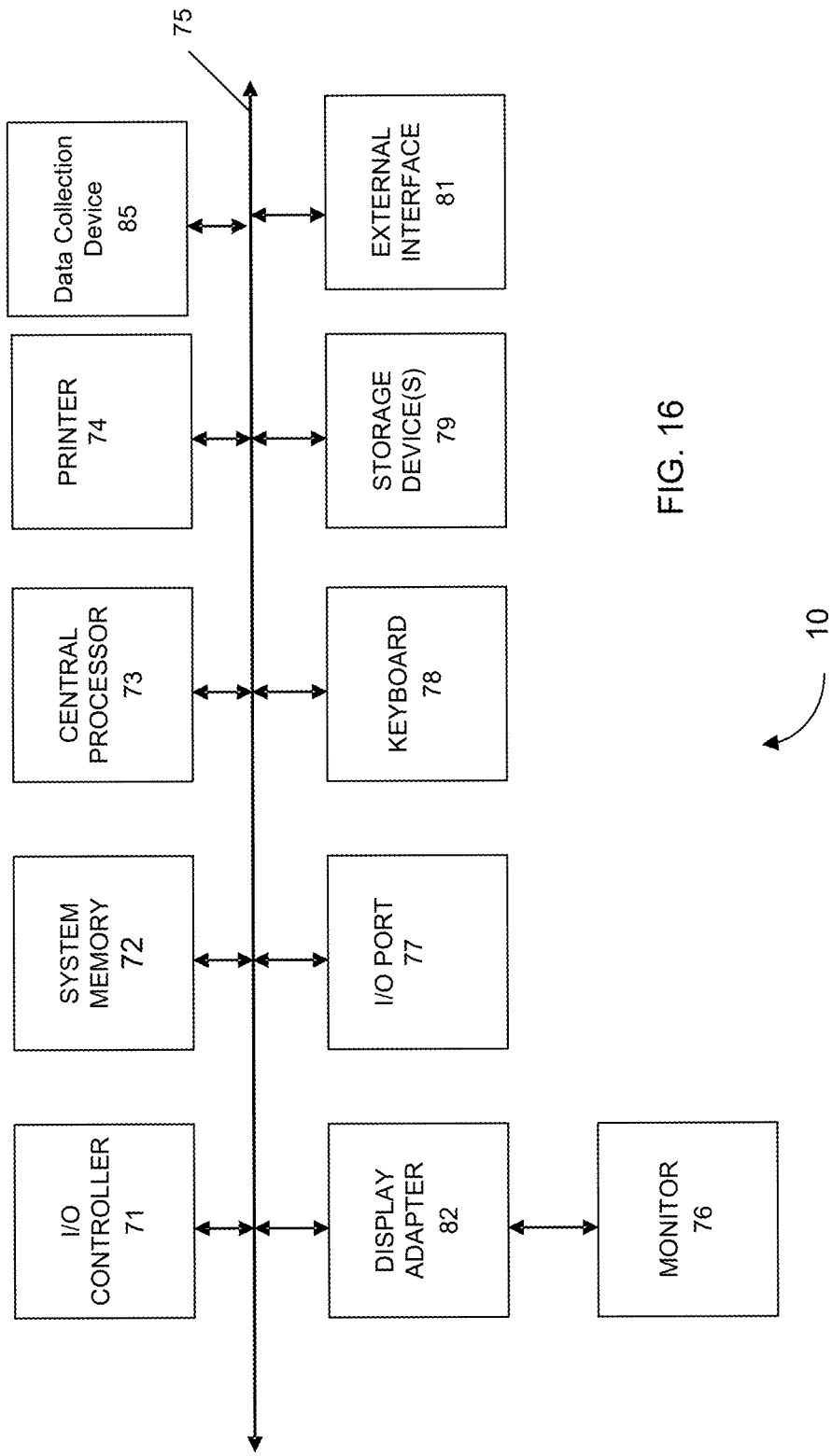
FIG. 16 shows a block diagram of an example computer system usable with system and methods according to embodiments of the present invention.

Any of the computer systems mentioned herein may utilize any suitable number of subsystems. Examples of such subsystems are shown in FIG. 16 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 6 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

IX. REFERENCES

1. Dondorp W, de Wert G, Bombard Y, Bianchi D W, Bergmann C, Borry P, et al. Non-invasive prenatal testing for aneuploidy and beyond: Challenges of responsible innovation in prenatal screening. Eur J Hum Genet 2015.
2. Chiu R W K, Chan K C A, Gao Y, Lau V Y M, Zheng W, Leung T Y, et al. Noninvasive prenatal diagnosis of fetal chromosomal aneuploidy by massively parallel genomic sequencing of dna in maternal plasma. Proc Natl Acad Sci USA 2008; 105:20458-63.
3. Jain M, Fiddes I T, Miga K H, Olsen H E, Paten B, Akeson M. Improved data analysis for the MinION nanopore sequencer. Nat Methods 2015; 12:351-6.
4. Lo Y M D, Chan K C A, Sun H, Chen E Z, Jiang P, Lun F M F, et al. Maternal plasma DNA sequencing reveals the genome-wide genetic and mutational profile of the fetus. Sci Transl Med 2010; 2:61ra91-61ra91.
5. Bayley H. Nanopore sequencing: From imagination to reality. Clin Chem 2015; 61:25-31.
6. Zheng Y W, Chan K C A, Sun H, Jiang P, Su X, Chen E Z, et al. Nonhematopoietically derived DNA is shorter than hematopoietically derived DNA in plasma: A transplantation model. Clin Chem 2012; 58:549-58.
7. Lun F M F, Chiu R W K, Sun K, Leung T Y, Jiang P, Chan K C A, et al. Noninvasive prenatal methylomic analysis by genomewide bisulfite sequencing of maternal plasma DNA. Clin Chem 2013; 59:1583-94.
8. Chan K C A, Jiang P, Zheng Y W, Liao G J W, Sun H, Wong J, et al. Cancer genome scanning in plasma: Detection of tumor-associated copy number aberrations, single-nucleotide variants, and tumoral heterogeneity by massively parallel sequencing. Clin Chem 2013; 59:211-24.
9. Chan K C A, Jiang P, Chan C W M, Sun K, Wong J, Hui E P, et al. Noninvasive detection of cancer-associated genome-wide hypomethylation and copy number aberrations by plasma DNA bisulfite sequencing. Proc Natl Acad Sci USA 2013; 110:18761-8.
10. Chan R W Y, Wong J, Chan H L Y, Mok T S K, Lo W Y W, Lee V, et al. Aberrant concentrations of liver-derived plasma albumin mrna in liver pathologies. Clin Chem 2010; 56:82-9.
11. Chan R W Y, Jiang P, Peng X, Tam L S, Liao G J W, Li E K, et al. Plasma DNA aberrations in systemic lupus erythematosus revealed by genomic and methylomic sequencing. Proc Natl Acad Sci USA 2014; 111:E5302-11.
12. Schreiber J, Wescoe Z L, Abu-Shumays R, Vivian J T, Baatar B, Karplus K, Akeson M. Error rates for nanopore discrimination among cytosine, methylcytosine, and hydroxymethylcytosine along individual DNA strands. Proc Natl Acad Sci USA 2013; 110:18910-5.

What is claimed is:
1. A method comprising:
   receiving a biological sample obtained from a single subject, the biological sample including a bodily fluid comprising cell-free DNA fragments;
   extracting a plurality of the cell-free DNA fragments from the biological sample;
   concatemerizing, in a container, a first set of the plurality of the cell-free DNA fragments to obtain a first concatemer consisting of the first set of the plurality of the cell-free DNA fragments and optionally spacer DNA fragments, wherein the cell-free DNA fragments of the first set have different sequences and are from different locations in the genome of the subject;

concatemerizing a second set of the plurality of the cell-free DNA fragments to obtain a second concatemer consisting of the second set of the plurality of the cell-free DNA fragments and optionally spacer DNA fragments, wherein the second concatemer comprises a different combination or a different permutation of the cell-free DNA fragments than the first concatemer, wherein concatemerizing the second set of the plurality of the cell-free DNA fragments occurs in parallel in the container with the concatemerizing of the first set of the plurality of the cell-free DNA fragments;

performing single-molecule sequencing of the first concatemer to obtain a first sequence, the first sequence including the different sequences of the first set of the plurality of the cell-free DNA fragments as subsequences within the first sequence; and performing single-molecule sequencing of the second concatemer to obtain a second sequence, the second sequence including the different sequences of the second set of the plurality of the cell-free DNA fragments as subsequences within the second sequence.

2. The method of claim 1, wherein performing single-molecule sequencing of the first concatemer comprises providing the first concatemer to a sequencing device, wherein the sequencing device includes a first nanopore, and the method further comprises:

passing the first concatemer through the first nanopore; and detecting first electrical signals as the first concatemer passes through the first nanopore, the first electrical signals corresponding to the first sequence of the first concatemer.

3. The method of claim 2, further comprising performing, by a computer system:

analyzing the first electrical signals to determine the first sequence; and aligning subsequences of the first sequence to a reference genome to identify fragment sequences corresponding to each of the first set of the plurality of the cell-free DNA fragments.

4. The method of claim 2, wherein passing the first concatemer through the first nanopore includes:

passing a first strand of the first concatemer through the first nanopore; and subsequently, passing a second strand of the first concatemer through the first nanopore.

5. The method of claim 4, further comprising analyzing, by a computer system, the first electrical signals for the first strand and the second strand to determine the first sequence.

6. The method of claim 2, wherein the first nanopore is one of a plurality of nanopores on a substrate.

7. The method of claim 6, further comprising:

passing the second concatemer through a second nanopore of the plurality of nanopores; and detecting a plurality of second electrical signals as the second concatemer passes through the second nanopore, the second electrical signals corresponding to the second sequence of the second concatemer.

8. The method of claim 1, further comprising:

hybridizing a fluorescent-labeled nucleotide to the first concatemer, and detecting a fluorescent signal, the fluorescent signal corresponding to a nucleotide.

9. The method of claim 1, further comprising performing, by a computer system:

aligning subsequences of the first sequence to a reference genome to identify fragment sequences corresponding to each of the first set of the plurality of the cell-free DNA fragments.

10. The method of claim 9, further comprising:

determining a size of each of the first set of the plurality of the cell-free DNA fragments based on the aligning of the subsequences of the first sequence, wherein the first sequence does not include spacer DNA fragments.

11. The method of claim 9, wherein:

concatemerizing the first set of the plurality of the cell-free DNA fragments comprises concatemerizing the first set of the plurality of the cell-free DNA fragments and the spacer DNA fragments, wherein the spacer DNA fragments are a set of DNA fragments having known sequences and wherein the set of DNA fragments having known sequences is interspersed among the first set of the plurality of the cell-free DNA fragments, and aligning subsequences of the first sequence comprises aligning subsequences to the known sequences to identify locations of the set of DNA fragments having known sequences in the first concatemer.

12. The method of claim 11, wherein the concatemerizing to form the first concatemer places one DNA fragment having a known sequence between two DNA fragments of the first set of the plurality of the cell-free DNA fragments.

13. The method of claim 12, further comprising performing, by the computer system:

identifying, by the computer system, a starting base of a first subsequence corresponding to a first DNA fragment of the first set of the plurality of the cell-free DNA fragments based on identifying one of the DNA fragments having a known sequence being before the first subsequence; and identifying, by the computer system, an ending base of the first subsequence corresponding to the first DNA fragment of the first set of the plurality of the cell-free DNA fragments based on identifying one of the DNA fragments having a known sequence being after the first subsequence.

14. The method of claim 11, wherein each known sequence of the set of DNA fragments having known sequences has a length of no more than seven nucleotides.

15. The method of claim 11, wherein each of the second set of the plurality of the cell-free DNA fragments has the same known sequence.

16. The method of claim 9, wherein the aligning of the subsequences includes:

aligning sliding windows of the first sequence to the reference genome, each sliding window corresponding to a subsequence that is being aligned to the reference genome; and identifying when two sliding windows align to different regions of the reference genome to distinguish between sequences of two DNA fragments of the first set of the plurality of the cell-free DNA fragments.

17. The method of claim 16, further comprising performing, by the computer system:

determine an ending or a beginning of a first subsequence of a first DNA fragment of the first set of the plurality of the cell-free DNA fragments based on the two sliding windows aligning to the different regions of the reference genome.

18. The method of claim 16, wherein the different regions of the reference genome comprise regions on different chromosomes.

19. The method of claim 16, wherein one or more windows between the two sliding windows are identified as not aligning to the reference genome.

20. The method of claim 19, further comprising determining the size of a first DNA fragment of the first set of the plurality of the cell-free DNA fragments, wherein determining the size of the first DNA fragment comprises:
determining a length of a longest subsequence that aligns to a single region of the reference genome.

21. The method of claim 1, wherein the biological sample is plasma or serum.

22. The method of claim 1, wherein the first set of the cell-free DNA fragments is randomly distributed from a plurality of chromosomes.

23. The method of claim 1, wherein the first concatemer does not include a spacer fragment having a known sequence between cell-free DNA fragments of the first set of the plurality of the cell-free DNA fragments.

24. The method of claim 1, wherein the first concatemer does not comprise replicated DNA fragments of the plurality of the cell-free DNA fragments, and the second concatemer does not comprise replicated DNA fragments of the plurality of the cell-free DNA fragments.

25. The method of claim 1 further comprising:
determining a size distribution of the plurality of the cell-free DNA fragments using the subsequences within the first sequence and the subsequences within the second sequence.

26. The method of claim 1, wherein the biological sample obtained from the single subject is maternal plasma comprising maternal cell-free DNA fragments and fetal cell-free DNA fragments from which the first set of the plurality of the cell-free DNA fragments and the second set of the plurality of the cell-free DNA fragments are obtained.

27. A method comprising:
receiving a biological sample obtained from a single subject, the biological sample including a bodily fluid comprising cell-free DNA fragments;
extracting a plurality of the cell-free DNA fragments from the biological sample;
concatemerizing a first set of the plurality of the cell-free DNA fragments to obtain a first concatemer consisting of the first set of the plurality of the cell-free DNA fragments and optionally spacer DNA fragments, wherein:
the cell-free DNA fragments of the first set have different sequences and are from different locations in the genome of the subject, and
the first concatemer does not comprise replicated DNA fragments of the plurality of the cell-free DNA fragments;
concatemerizing a second set of the plurality of the cell-free DNA fragments to obtain a second concatemer consisting of the second set of the plurality of the cell-free DNA fragments and optionally spacer DNA fragments, wherein the second concatemer comprises a different combination or a different permutation of the cell-free DNA fragments than the first concatemer, wherein:
concatemerizing the second set of the plurality of the cell-free DNA fragments occurs in parallel with the concatemerizing of the first set of the plurality of the cell-free DNA fragments, and
the second concatemer does not comprise replicated DNA fragments of the plurality of the cell-free DNA fragments;
performing single-molecule sequencing of the first concatemer to obtain a first sequence, the first sequence including the different sequences of the first set of the plurality of the cell-free DNA fragments as subsequences within the first sequence; and
performing single-molecule sequencing of the second concatemer to obtain a second sequence, the second sequence including the different sequences of the second set of the plurality of the cell-free DNA fragments as subsequences within the second sequence.

* * * * *